(12) United States Patent
Lenser et al.

(10) Patent No.: US 11,877,914 B2
(45) Date of Patent: *Jan. 23, 2024

(54) METHOD AND APPARATUS FOR ASSEMBLING ABSORBENT ARTICLES

(71) Applicant: The Procter & Gamble Company, Cincinnati, OH (US)

(72) Inventors: Todd Douglas Lenser, Liberty Township, OH (US); Urmish Popatlal Dalal, Milford, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/099,298

(22) Filed: Jan. 20, 2023

(65) Prior Publication Data
US 2023/0157900 A1    May 25, 2023

Related U.S. Application Data

(63) Continuation of application No. 17/830,452, filed on Jun. 2, 2022, now Pat. No. 11,596,557, which is a
(Continued)

(51) Int. Cl.
*B29C 65/08* (2006.01)
*A61F 13/15* (2006.01)
(Continued)

(52) U.S. Cl.
CPC .. *A61F 13/15699* (2013.01); *A61F 13/15593* (2013.01); *A61F 13/15601* (2013.01);
(Continued)

(58) Field of Classification Search
CPC .......... A61F 13/15699; A61F 13/15739; A61F 13/15764; B29C 65/08; B29C 65/74;
(Continued)

(56) References Cited

U.S. PATENT DOCUMENTS 3,113,225 A    12/1963   Claus
3,338,992 A    8/1967    Allison
(Continued)

FOREIGN PATENT DOCUMENTS

CN    101170977 A    4/2008
CN    103209828 A    7/2013
(Continued)

OTHER PUBLICATIONS

14424 PCT Search Report and Written Opinion for PCT/US2017/046388 dated Sep. 22, 2017, 13 pages.
(Continued)

*Primary Examiner* — James D Sells
(74) *Attorney, Agent, or Firm* — Daniel S. Albrecht; Sarah M. DeCristofaro

(57) ABSTRACT

The present disclosure relates to assembling elastic laminates that may be used to make absorbent article components. Methods herein may include an anvil adapted to rotate about an axis of rotation, wherein first and second spreader mechanisms adjacent the anvil roll are axially and angularly displaced from each other with respect to the axis of rotation. During the assembly process, a substrate may be advanced in a machine direction onto the rotating anvil. The first spreader mechanism stretches a first elastic material in the cross direction, and the second spreader mechanism stretches a second elastic material in the cross direction. The stretched first and second elastic materials advance from the spreader mechanisms and onto the substrate on the anvil roll. The combined and elastic materials may then be ultrasonically bonded together on the anvil to form at least one elastic laminate.

20 Claims, 17 Drawing Sheets

Related U.S. Application Data continuation of application No. 17/350,240, filed on Jun. 17, 2021, now Pat. No. 11,382,798, which is a continuation of application No. 16/740,814, filed on Jan. 13, 2020, now Pat. No. 11,071,654, which is a continuation of application No. 15/674,563, filed on Aug. 11, 2017, now Pat. No. 10,568,775.

(60) Provisional application No. 62/419,515, filed on Nov. 9, 2016, provisional application No. 62/406,025, filed on Oct. 10, 2016, provisional application No. 62/374,010, filed on Aug. 12, 2016.

(51) Int. Cl.

| | | |
|---|---|---|
| *B32B 7/05* | (2019.01) | |
| *A61F 13/49* | (2006.01) | |
| *B29C 55/02* | (2006.01) | |
| *B29C 65/74* | (2006.01) | |
| *B29C 65/00* | (2006.01) | |
| *B32B 5/02* | (2006.01) | |
| *B32B 37/10* | (2006.01) | |
| *B32B 37/14* | (2006.01) | |
| *B32B 38/00* | (2006.01) | |
| *B32B 27/12* | (2006.01) | |
| B32B 15/09 | (2006.01) | |
| B32B 27/30 | (2006.01) | |
| B29C 65/78 | (2006.01) | |
| *B32B 7/04* | (2019.01) | |
| B32B 27/06 | (2006.01) | |
| B32B 27/40 | (2006.01) | |
| B32B 5/22 | (2006.01) | |
| B32B 27/34 | (2006.01) | |
| B32B 15/088 | (2006.01) | |
| B32B 27/28 | (2006.01) | |
| B32B 15/095 | (2006.01) | |
| B32B 15/14 | (2006.01) | |
| B32B 15/082 | (2006.01) | |
| B32B 15/04 | (2006.01) | |
| B32B 5/26 | (2006.01) | |
| B29C 55/08 | (2006.01) | |
| B32B 3/08 | (2006.01) | |
| B32B 15/08 | (2006.01) | |
| B32B 37/20 | (2006.01) | |
| B32B 38/18 | (2006.01) | |
| B32B 15/06 | (2006.01) | |
| B32B 25/14 | (2006.01) | |
| B32B 27/36 | (2006.01) | |
| B32B 27/08 | (2006.01) | |
| B29K 21/00 | (2006.01) | |
| B29L 9/00 | (2006.01) | |
| B29L 31/48 | (2006.01) | |

(52) U.S. Cl.
CPC .. *A61F 13/15609* (2013.01); *A61F 13/15674* (2013.01); *A61F 13/15723* (2013.01); *A61F 13/15731* (2013.01); *A61F 13/15739* (2013.01); *A61F 13/15764* (2013.01); *A61F 13/49009* (2013.01); *A61F 13/49012* (2013.01); *A61F 13/49019* (2013.01); *B29C 55/02* (2013.01); *B29C 65/08* (2013.01); *B29C 65/74* (2013.01); *B29C 66/00145* (2013.01); *B29C 66/43* (2013.01); *B29C 66/4722* (2013.01); *B29C 66/83413* (2013.01); *B32B 5/022* (2013.01); *B32B 7/05* (2019.01); *B32B 27/12* (2013.01); *B32B 37/1018* (2013.01); *B32B 37/14* (2013.01); *B32B 38/0012* (2013.01); *A61F 2013/15715* (2013.01); *A61F 2013/15869* (2013.01); *A61F 2013/15926* (2013.01); *A61F 2013/49093* (2013.01); *B29C 55/08* (2013.01); *B29C 65/086* (2013.01); *B29C 65/7847* (2013.01); *B29C 66/1122* (2013.01); *B29C 66/21* (2013.01); *B29C 66/344* (2013.01); *B29C 66/433* (2013.01); *B29C 66/723* (2013.01); *B29C 66/7294* (2013.01); *B29C 66/81469* (2013.01); *B29C 66/83411* (2013.01); *B29C 66/83415* (2013.01); *B29K 2021/003* (2013.01); *B29K 2995/0046* (2013.01); *B29L 2009/00* (2013.01); *B29L 2031/4878* (2013.01); *B32B 3/08* (2013.01); *B32B 5/22* (2013.01); *B32B 5/26* (2013.01); *B32B 7/04* (2013.01); *B32B 15/04* (2013.01); *B32B 15/043* (2013.01); *B32B 15/06* (2013.01); *B32B 15/08* (2013.01); *B32B 15/082* (2013.01); *B32B 15/088* (2013.01); *B32B 15/09* (2013.01); *B32B 15/095* (2013.01); *B32B 15/14* (2013.01); *B32B 25/14* (2013.01); *B32B 27/06* (2013.01); *B32B 27/08* (2013.01); *B32B 27/285* (2013.01); *B32B 27/302* (2013.01); *B32B 27/34* (2013.01); *B32B 27/36* (2013.01); *B32B 27/40* (2013.01); *B32B 37/144* (2013.01); *B32B 37/20* (2013.01); *B32B 38/1858* (2013.01); *B32B 2038/0028* (2013.01); *B32B 2262/0207* (2013.01); *B32B 2262/14* (2013.01); *B32B 2270/00* (2013.01); *B32B 2274/00* (2013.01); *B32B 2307/51* (2013.01); *B32B 2307/718* (2013.01); *B32B 2307/732* (2013.01); *B32B 2555/02* (2013.01); *B32B 2556/00* (2013.01)

(58) Field of Classification Search
CPC ........ B29C 66/7294; B29K 2995/0046; B29L 2009/00; B29L 2031/4878
USPC ...................................................... 156/580.1
See application file for complete search history.

(56) References Cited

U.S. PATENT DOCUMENTS

| | | |
|---|---|---|
| 3,562,041 A | 2/1971 | Robertson |
| 3,566,726 A | 3/1971 | Politis |
| 3,692,613 A | 9/1972 | Pederson |
| 3,733,238 A | 5/1973 | Long |
| 3,802,817 A | 4/1974 | Matsuki |
| 3,848,594 A | 11/1974 | Buell |
| 3,849,241 A | 11/1974 | Butin |
| 3,860,003 A | 1/1975 | Buell |
| 3,911,173 A | 10/1975 | Sprague, Jr. |
| 3,929,135 A | 12/1975 | Thompson |
| 4,116,892 A | 9/1978 | Schwarz |
| 4,324,314 A | 4/1982 | Beach et al. |
| 4,405,297 A | 9/1983 | Appel |
| 4,463,045 A | 7/1984 | Ahr et al. |
| 4,515,595 A | 5/1985 | Kievit |
| 4,573,986 A | 3/1986 | Minetola et al. |
| 4,610,678 A | 9/1986 | Weisman |
| 4,629,643 A | 12/1986 | Curro |
| 4,634,440 A | 1/1987 | Widlund |
| 4,662,875 A | 5/1987 | Hirotsu |
| 4,673,402 A | 6/1987 | Weisman |
| 4,699,622 A | 10/1987 | Toussant |
| 4,710,189 A | 12/1987 | Lash |
| 4,780,352 A | 10/1988 | Palumbo |
| 4,785,996 A | 11/1988 | Ziecker et al. |
| 4,834,735 A | 5/1989 | Alemany |
| 4,834,741 A | 5/1989 | Sabee |
| 4,842,666 A | 6/1989 | Werenicz |

(56) References Cited

U.S. PATENT DOCUMENTS

| | | |
|---|---|---|
| 4,846,815 A | 7/1989 | Scripps |
| 4,854,984 A | 8/1989 | Ball |
| 4,888,231 A | 12/1989 | Angstadt |
| 4,892,536 A | 1/1990 | DesMarais et al. |
| 4,894,060 A | 1/1990 | Nestegard |
| 4,919,738 A | 4/1990 | Ball et al. |
| 4,940,464 A | 7/1990 | Van Gompel et al. |
| 4,946,527 A | 8/1990 | Battrell |
| 4,990,147 A | 2/1991 | Freeland |
| 5,006,394 A | 4/1991 | Baird |
| 5,037,416 A | 8/1991 | Allen |
| 5,092,861 A | 3/1992 | Nomura |
| 5,137,537 A | 8/1992 | Herron |
| 5,143,679 A | 9/1992 | Weber |
| 5,147,345 A | 9/1992 | Lavon |
| 5,149,720 A | 9/1992 | Desmarais |
| 5,151,092 A | 9/1992 | Buell |
| 5,156,793 A | 10/1992 | Buell |
| 5,167,897 A | 12/1992 | Weber et al. |
| 5,221,274 A | 6/1993 | Buell |
| 5,242,436 A | 9/1993 | Weil |
| 5,246,433 A | 9/1993 | Hasse |
| 5,260,345 A | 11/1993 | Desmarais |
| 5,266,392 A | 11/1993 | Land |
| 5,269,775 A | 12/1993 | Freeland |
| 5,342,338 A | 8/1994 | Roe |
| 5,344,691 A | 9/1994 | Hanschen |
| 5,360,420 A | 11/1994 | Cook et al. |
| 5,376,430 A | 12/1994 | Swenson et al. |
| 5,382,400 A | 1/1995 | Pike |
| 5,387,207 A | 2/1995 | Dyer |
| 5,397,316 A | 3/1995 | Young |
| 5,418,045 A | 5/1995 | Pike |
| 5,422,172 A | 6/1995 | Wu |
| 5,433,715 A | 7/1995 | Tanzer |
| 5,518,801 A | 5/1996 | Chappell et al. |
| 5,554,145 A | 9/1996 | Roe |
| 5,569,234 A | 10/1996 | Buell |
| 5,571,096 A | 11/1996 | Dobrin |
| 5,580,411 A | 12/1996 | Nease |
| 5,591,155 A | 1/1997 | Nishikawa |
| 5,599,335 A | 2/1997 | Goldman et al. |
| 5,607,414 A | 3/1997 | Richards |
| 5,607,760 A | 3/1997 | Roe |
| 5,609,587 A | 3/1997 | Roe |
| 5,622,772 A | 4/1997 | Stokes |
| 5,628,097 A | 5/1997 | Benson |
| 5,635,191 A | 6/1997 | Roe |
| 5,643,588 A | 7/1997 | Roe |
| 5,658,639 A | 8/1997 | Curro |
| 5,665,300 A | 9/1997 | Brignola |
| 5,674,216 A | 10/1997 | Buell et al. |
| 5,691,034 A | 11/1997 | Krueger |
| 5,700,254 A | 12/1997 | McDowall et al. |
| 5,702,551 A | 12/1997 | Huber et al. |
| 5,707,468 A | 1/1998 | Arnold |
| 5,804,021 A | 9/1998 | Abuto et al. |
| 5,817,199 A | 10/1998 | Brennecke et al. |
| 5,827,909 A | 10/1998 | Desmarais |
| 5,865,823 A | 2/1999 | Curro |
| 5,897,545 A | 4/1999 | Kline |
| 5,916,661 A | 6/1999 | Benson |
| 5,957,908 A | 9/1999 | Kline |
| 5,968,025 A | 10/1999 | Roe |
| 5,968,888 A | 10/1999 | Blandiaux |
| 5,972,806 A | 10/1999 | Weinberger |
| 5,993,432 A | 11/1999 | Lodge |
| 6,004,306 A | 12/1999 | Robles |
| 6,030,373 A | 2/2000 | Vangompel |
| 6,036,796 A | 3/2000 | Halbert |
| 6,096,668 A | 8/2000 | Abuto |
| 6,107,537 A | 8/2000 | Elder |
| 6,118,041 A | 9/2000 | Roe et al. |
| 6,120,487 A | 9/2000 | Ashton |
| 6,120,489 A | 9/2000 | Johnson |
| 6,123,792 A | 9/2000 | Samida |
| 6,140,551 A | 10/2000 | Niemeyer |
| 6,153,209 A | 11/2000 | Vega et al. |
| 6,169,151 B1 | 1/2001 | Waymouth |
| 6,255,236 B1 | 7/2001 | Cree |
| 6,310,154 B1 | 10/2001 | Babcock |
| 6,369,121 B1 | 4/2002 | Catalfamo |
| 6,410,129 B2 | 6/2002 | Zhang |
| 6,426,444 B2 | 7/2002 | Roe et al. |
| 6,428,526 B1 | 8/2002 | Heindel |
| 6,432,098 B1 | 8/2002 | Kline |
| 6,454,989 B1 | 9/2002 | Neely |
| 6,458,447 B1 | 10/2002 | Cabell |
| 6,465,073 B1 | 10/2002 | Morman |
| 6,472,045 B1 | 10/2002 | Morman |
| 6,472,084 B1 | 10/2002 | Middlesworth |
| 6,475,600 B1 | 11/2002 | Morman |
| 6,498,284 B1 | 12/2002 | Roe |
| 6,508,641 B1 | 1/2003 | Kubik |
| 6,513,221 B2 | 2/2003 | Vogt |
| 6,518,378 B2 | 2/2003 | Waymouth |
| 6,534,149 B1 | 3/2003 | Daley |
| 6,540,854 B2 | 4/2003 | Couillard |
| 6,551,294 B1 | 4/2003 | Elsberg et al. |
| 6,555,643 B1 | 4/2003 | Rieger |
| 6,559,262 B1 | 5/2003 | Waymouth |
| 6,572,595 B1 | 6/2003 | Klemp |
| 6,572,598 B1 | 6/2003 | Ashton |
| 6,586,652 B1 | 7/2003 | Warner et al. |
| 6,610,390 B1 | 8/2003 | Kauschke |
| 6,617,016 B2 | 9/2003 | Zhang et al. |
| 6,627,564 B1 | 9/2003 | Morman |
| 6,627,787 B1 | 9/2003 | Roe et al. |
| 6,632,386 B2 | 10/2003 | Shelley |
| 6,645,330 B2 | 11/2003 | Pargass |
| 6,645,569 B2 | 11/2003 | Cramer et al. |
| 6,649,001 B2 | 11/2003 | Heden |
| 6,677,258 B2 | 1/2004 | Carroll |
| 6,692,477 B2 | 2/2004 | Gibbs |
| 6,713,159 B1 | 3/2004 | Blenke |
| 6,758,925 B1 | 7/2004 | Stegelmann |
| 6,767,420 B2 | 7/2004 | Stegelmann |
| 6,818,083 B2 | 11/2004 | Mcamish et al. |
| 6,825,393 B2 | 11/2004 | Roe et al. |
| 6,830,800 B2 | 12/2004 | Curro |
| 6,843,134 B2 | 1/2005 | Anderson |
| 6,849,142 B1 | 2/2005 | Goulait |
| 6,861,571 B1 | 3/2005 | Roe et al. |
| 6,863,933 B2 | 3/2005 | Cramer et al. |
| 6,878,433 B2 | 4/2005 | Curro |
| 6,905,488 B2 | 6/2005 | Olson |
| 6,974,514 B2 | 12/2005 | Hamulski |
| 7,056,404 B2 | 6/2006 | Mcfall |
| 7,062,983 B2 | 6/2006 | Anderson |
| 7,108,759 B2 | 9/2006 | You |
| 7,112,621 B2 | 9/2006 | Rohrbaugh et al. |
| 7,270,861 B2 | 9/2007 | Broering |
| 7,291,239 B2 | 11/2007 | Polanco |
| 7,435,243 B2 | 10/2008 | Miyamoto |
| 7,531,233 B2 | 5/2009 | Kling |
| 7,569,039 B2 | 8/2009 | Matsuda |
| 7,572,249 B2 | 8/2009 | Betts |
| 7,582,075 B2 | 9/2009 | Betts |
| 7,625,363 B2 | 12/2009 | Yoshimasa |
| 7,741,235 B2 | 6/2010 | Hashimoto |
| 7,803,244 B2 | 9/2010 | Siqueira |
| 7,806,883 B2 | 10/2010 | Fossum |
| 7,819,853 B2 | 10/2010 | Desai |
| 7,824,594 B2 | 11/2010 | Qureshi |
| 7,870,651 B2 | 1/2011 | Middlesworth |
| 7,896,641 B2 | 3/2011 | Qureshi |
| 7,917,985 B2 | 4/2011 | Dorsey |
| 7,931,632 B2 | 4/2011 | Betts |
| 7,954,213 B2 | 6/2011 | Mizutani |
| 7,998,127 B2 | 8/2011 | Betts |
| 8,062,279 B2 | 11/2011 | Miyamoto |
| 8,062,572 B2 | 11/2011 | Qureshi |
| 8,092,438 B2 | 1/2012 | Betts |
| 8,118,801 B2 | 2/2012 | Macura |

(56) References Cited

U.S. PATENT DOCUMENTS

| | | |
|---|---|---|
| 8,158,043 B2 | 4/2012 | Gibson |
| 8,172,971 B2 | 5/2012 | Yamamoto |
| 8,186,296 B2 | 5/2012 | Brown et al. |
| 8,361,913 B2 | 1/2013 | Siqueira |
| 8,450,557 B2 | 5/2013 | Nishitani |
| 8,454,571 B2 | 6/2013 | Rezai |
| 8,480,642 B2 | 7/2013 | Betts |
| 8,491,557 B2 | 7/2013 | Kline |
| 8,491,742 B2 | 7/2013 | Waas |
| 8,496,775 B2 | 7/2013 | Deng |
| 8,502,013 B2 | 8/2013 | Zhao |
| 8,518,004 B2 | 8/2013 | Betts |
| 8,585,666 B2 | 11/2013 | Weisman |
| 8,618,350 B2 | 12/2013 | Mansfield |
| 8,679,391 B2 | 3/2014 | Odonnell |
| 8,690,852 B2 | 4/2014 | Macura |
| 8,697,938 B2 | 4/2014 | Roe |
| 8,709,579 B2 | 4/2014 | Hoenigmann |
| 8,728,051 B2 | 5/2014 | Lu |
| 8,741,083 B2 | 6/2014 | Wennerback |
| 8,776,856 B2 | 7/2014 | Yamamoto |
| 8,795,809 B2 | 8/2014 | Mansfield |
| 8,858,523 B2 | 10/2014 | Sauer |
| 8,939,957 B2 | 1/2015 | Raycheck |
| 8,940,116 B2 | 1/2015 | Gilgenbach |
| 9,102,132 B2 | 8/2015 | Wennerbck |
| 9,169,384 B2 | 10/2015 | Autran |
| 9,211,221 B2 | 12/2015 | Macura |
| 9,301,889 B2 | 4/2016 | Miyamoto |
| 9,333,125 B2 | 5/2016 | Kline et al. |
| 9,358,161 B2 | 6/2016 | Lawson |
| 9,434,143 B2 | 9/2016 | Sablone |
| 9,498,941 B2 | 11/2016 | Sablone |
| 9,533,067 B2 | 1/2017 | Schonbeck |
| 9,687,580 B2 | 6/2017 | Schonbeck |
| 9,724,248 B2 | 8/2017 | Hughes |
| 9,821,542 B2 | 11/2017 | Bruce |
| 10,485,713 B2 | 11/2019 | Schonbeck |
| 10,524,964 B2 | 1/2020 | Sauer |
| 10,561,537 B2 | 2/2020 | Lenser et al. |
| 10,568,775 B2 | 2/2020 | Lenser |
| 10,568,776 B2 | 2/2020 | Lenser |
| 10,575,993 B2 | 3/2020 | Lenser |
| 10,588,789 B2 | 3/2020 | Surushe |
| 10,617,573 B2 | 4/2020 | Koshijima |
| 10,799,396 B2 | 10/2020 | Takeuchi |
| 10,959,887 B2 | 3/2021 | Lenser et al. |
| 10,966,876 B2 | 4/2021 | Lenser et al. |
| 11,071,654 B2 | 7/2021 | Lenser et al. |
| 11,083,633 B2 | 8/2021 | Lenser et al. |
| 11,135,100 B2 | 10/2021 | Schönbeck et al. |
| 11,179,278 B2 | 11/2021 | Schönbeck et al. |
| 11,266,543 B2 | 3/2022 | Lenser et al. |
| 11,331,223 B2 | 5/2022 | Lenser et al. |
| 11,382,798 B2 | 7/2022 | Lenser et al. |
| 11,642,250 B2 * | 5/2023 | Lenser .............. A61F 13/49019 156/73.1 |
| 2001/0018579 A1 | 8/2001 | Klemp |
| 2001/0024940 A1 | 9/2001 | Cook et al. |
| 2002/0095129 A1 | 7/2002 | Friderich |
| 2002/0187696 A1 | 12/2002 | Veiga et al. |
| 2002/0188268 A1 | 12/2002 | Kline |
| 2003/0021951 A1 | 1/2003 | Desai |
| 2003/0105446 A1 | 6/2003 | Hutson |
| 2003/0109843 A1 | 6/2003 | Gibbs |
| 2003/0109844 A1 | 6/2003 | Gibbs |
| 2003/0120240 A1 | 6/2003 | Buell |
| 2003/0124310 A1 | 7/2003 | Ellis |
| 2003/0148684 A1 | 8/2003 | Cramer et al. |
| 2003/0181120 A1 | 9/2003 | Wu |
| 2003/0233082 A1 | 12/2003 | Kline |
| 2004/0087235 A1 | 5/2004 | Morman |
| 2004/0091693 A1 | 5/2004 | Thomas |
| 2004/0102125 A1 | 5/2004 | Morman |
| 2004/0112509 A1 | 6/2004 | Morman |
| 2004/0121690 A1 | 6/2004 | Mleziva |
| 2004/0182499 A1 | 9/2004 | Collier |
| 2004/0209042 A1 | 10/2004 | Peacock |
| 2004/0224132 A1 | 11/2004 | Roe |
| 2005/0008839 A1 | 1/2005 | Cramer et al. |
| 2005/0065487 A1 | 3/2005 | Graef |
| 2005/0107764 A1 | 5/2005 | Matsuda et al. |
| 2005/0154362 A1 | 7/2005 | Warren |
| 2005/0222546 A1 | 10/2005 | Vargo |
| 2005/0245162 A1 | 11/2005 | Mccormack |
| 2005/0287892 A1 | 12/2005 | Fouse |
| 2006/0062963 A1 | 3/2006 | Middlesworth |
| 2006/0089616 A1 | 4/2006 | Belau et al. |
| 2006/0135024 A1 | 6/2006 | Thomas |
| 2006/0148361 A1 | 7/2006 | Mccormack |
| 2006/0149209 A1 | 7/2006 | Malchow |
| 2006/0271003 A1 | 11/2006 | Loescher |
| 2006/0287637 A1 | 12/2006 | Lam |
| 2007/0105472 A1 | 5/2007 | Marche |
| 2007/0123124 A1 | 5/2007 | Middlesworth |
| 2007/0141311 A1 | 6/2007 | Mleziva |
| 2007/0142798 A1 | 6/2007 | Goodlander |
| 2007/0142806 A1 | 6/2007 | Roe et al. |
| 2007/0142825 A1 | 6/2007 | Prisco |
| 2007/0143972 A1 | 6/2007 | Kline |
| 2007/0202767 A1 | 8/2007 | Anderson |
| 2007/0219521 A1 | 9/2007 | Hird |
| 2007/0234529 A1 | 10/2007 | Middlesworth |
| 2007/0237924 A1 | 10/2007 | Bruce |
| 2007/0249254 A1 | 10/2007 | Mansfield |
| 2007/0254176 A1 | 11/2007 | Patel |
| 2007/0254547 A1 | 11/2007 | Ducauchuis |
| 2007/0287983 A1 | 12/2007 | Lodge |
| 2008/0003910 A1 | 1/2008 | Hughes |
| 2008/0003911 A1 | 1/2008 | Sabbagh |
| 2008/0045917 A1 | 2/2008 | Autran |
| 2008/0051748 A1 | 2/2008 | Black |
| 2008/0076315 A1 | 3/2008 | Mccormack |
| 2008/0114325 A1 | 5/2008 | Edwall et al. |
| 2008/0119102 A1 | 5/2008 | Hughes |
| 2008/0147031 A1 | 6/2008 | Long |
| 2008/0241476 A1 | 10/2008 | Olguin |
| 2008/0305298 A1 | 12/2008 | Lakshmi |
| 2008/0312622 A1 | 12/2008 | Hundorf |
| 2009/0035527 A1 | 2/2009 | Kobayashi |
| 2009/0069772 A1 | 3/2009 | Sauer |
| 2009/0069778 A1 | 3/2009 | Sauer |
| 2009/0191779 A1 | 7/2009 | Cree |
| 2009/0240222 A1 | 9/2009 | Tomoko |
| 2009/0258210 A1 | 10/2009 | Iyad |
| 2009/0275909 A1 | 11/2009 | Sakaguchi |
| 2009/0292266 A1 | 11/2009 | Back |
| 2009/0294044 A1 | 12/2009 | Gill |
| 2009/0299318 A1 | 12/2009 | Faulks |
| 2009/0299322 A1 | 12/2009 | Faulks |
| 2009/0325447 A1 | 12/2009 | Austin |
| 2009/0325448 A1 | 12/2009 | Welch |
| 2009/0326503 A1 | 12/2009 | Lakso |
| 2010/0018579 A1 | 1/2010 | Curran |
| 2010/0062231 A1 | 3/2010 | Abed |
| 2010/0076390 A1 | 3/2010 | Norrby |
| 2010/0090363 A1 | 4/2010 | Larsen |
| 2010/0104830 A1 | 4/2010 | Jaeger |
| 2010/0112313 A1 | 5/2010 | Nakakado |
| 2010/0168704 A1 | 7/2010 | Thomas |
| 2010/0262105 A1 | 10/2010 | Turner |
| 2010/0262107 A1 | 10/2010 | Turner et al. |
| 2010/0268183 A1 | 10/2010 | Een |
| 2010/0280481 A1 | 11/2010 | Kline |
| 2010/0280484 A1 | 11/2010 | Kline et al. |
| 2010/0285286 A1 | 11/2010 | Middlesworth |
| 2011/0004176 A1 | 1/2011 | Andersson |
| 2011/0040273 A1 | 2/2011 | Sablone |
| 2011/0046594 A1 | 2/2011 | Sablone |
| 2011/0139657 A1 | 6/2011 | Hird |
| 2011/0139658 A1 | 6/2011 | Hird |
| 2011/0139659 A1 | 6/2011 | Hird |
| 2011/0144610 A1 | 6/2011 | Karlson |
| 2011/0151739 A1 | 6/2011 | Bosler |

(56) References Cited

U.S. PATENT DOCUMENTS

| | | |
|---|---|---|
| 2011/0152812 A1 | 6/2011 | Hird |
| 2011/0178490 A1 | 7/2011 | Lavon |
| 2011/0196332 A1 | 8/2011 | Cheng |
| 2011/0318987 A1 | 12/2011 | Ooishi |
| 2012/0022490 A1 | 1/2012 | Marche et al. |
| 2012/0045620 A1 | 2/2012 | Oba |
| 2012/0055613 A1 | 3/2012 | Baeck |
| 2012/0055615 A1 | 3/2012 | Baeck |
| 2012/0061015 A1 | 3/2012 | Lavon et al. |
| 2012/0061016 A1 | 3/2012 | Lavon et al. |
| 2012/0095429 A1 | 4/2012 | Kobayashi |
| 2012/0100351 A1 | 4/2012 | Covelli |
| 2012/0116342 A1 | 5/2012 | Stjernholm |
| 2012/0141742 A1 | 6/2012 | Yamaguchi |
| 2012/0143165 A1 | 6/2012 | Macura |
| 2012/0168063 A1 | 7/2012 | Beuther |
| 2012/0196091 A1 | 8/2012 | Mizutani |
| 2012/0209230 A1 | 8/2012 | Mansfield |
| 2012/0238980 A1 | 9/2012 | Lam |
| 2012/0251771 A1 | 10/2012 | Wilson |
| 2012/0252716 A1 | 10/2012 | Barnabas et al. |
| 2012/0277713 A1 | 11/2012 | Raycheck |
| 2012/0316526 A1 | 12/2012 | Rosati et al. |
| 2012/0321839 A1 | 12/2012 | Uematsu |
| 2013/0017370 A1 | 1/2013 | Yamaguchi |
| 2013/0022784 A1 | 1/2013 | Uematsu |
| 2013/0072887 A1 | 3/2013 | Lavon |
| 2013/0082418 A1 | 4/2013 | Curro |
| 2013/0090623 A1 | 4/2013 | Ohashi |
| 2013/0095279 A1 | 4/2013 | Hauschildt |
| 2013/0144245 A1 | 6/2013 | Roe |
| 2013/0158497 A1 | 6/2013 | Yamaguchi |
| 2013/0164480 A1 | 6/2013 | Sakurai |
| 2013/0165883 A1 | 6/2013 | Kimura |
| 2013/0178815 A1 | 7/2013 | Ohashi |
| 2013/0184665 A1 | 7/2013 | Kato |
| 2013/0211356 A1 | 8/2013 | Nishikawa et al. |
| 2013/0213547 A1 | 8/2013 | Schneider |
| 2013/0218116 A1 | 8/2013 | Schneider |
| 2013/0230700 A1 | 9/2013 | Schoenbeck |
| 2013/0236700 A1 | 9/2013 | Yamanaka |
| 2013/0255861 A1 | 10/2013 | Schneider |
| 2013/0255862 A1 | 10/2013 | Schneider et al. |
| 2013/0255863 A1 | 10/2013 | Lavon et al. |
| 2013/0255864 A1 | 10/2013 | Schneider et al. |
| 2013/0255865 A1 | 10/2013 | Brown et al. |
| 2013/0280481 A1 | 10/2013 | Mitsuno |
| 2013/0284850 A1 | 10/2013 | Lenser |
| 2013/0306226 A1 | 11/2013 | Zink |
| 2014/0005628 A1 | 1/2014 | Lavon et al. |
| 2014/0018222 A1 | 1/2014 | Sablone |
| 2014/0018759 A1 | 1/2014 | Jayasinghe |
| 2014/0039434 A1 | 2/2014 | Xu |
| 2014/0041786 A1 | 2/2014 | Henke |
| 2014/0135194 A1 | 5/2014 | Sablone |
| 2014/0148774 A1 | 5/2014 | Brown |
| 2014/0163500 A1 | 6/2014 | Roe |
| 2014/0163506 A1 | 6/2014 | Roe |
| 2014/0163511 A1 | 6/2014 | Roe et al. |
| 2014/0234575 A1 | 8/2014 | Mitsuno |
| 2014/0276525 A1 | 9/2014 | Lavon et al. |
| 2014/0330232 A1 | 11/2014 | Schönbeck |
| 2014/0367032 A1 | 12/2014 | Homoelle et al. |
| 2014/0377506 A1 | 12/2014 | Eckstein et al. |
| 2014/0377513 A1 | 12/2014 | Galie |
| 2014/0378924 A1 | 12/2014 | Turner |
| 2015/0032078 A1 | 1/2015 | Collins |
| 2015/0038929 A1 | 2/2015 | Van Malderen |
| 2015/0057630 A1 | 2/2015 | Tange |
| 2015/0126955 A1 | 5/2015 | Sauer |
| 2015/0147530 A1 | 5/2015 | Mitsuno |
| 2015/0147539 A1 | 5/2015 | Thomas |
| 2015/0164699 A1 | 6/2015 | Schmitz |
| 2015/0164705 A1 | 6/2015 | Thomas |
| 2015/0173961 A1 | 6/2015 | Powell |
| 2015/0202091 A1 | 7/2015 | Sablone |
| 2015/0297419 A1 | 10/2015 | Nelson |
| 2015/0297421 A1 | 10/2015 | Nelson |
| 2015/0313774 A1 | 11/2015 | Homoelle |
| 2016/0008184 A1 | 1/2016 | Raycheck et al. |
| 2016/0013614 A1 | 1/2016 | Moto |
| 2016/0100999 A1 | 4/2016 | Hamilton |
| 2016/0136014 A1 | 5/2016 | Arora |
| 2016/0167334 A1 | 6/2016 | Arora |
| 2016/0206485 A1 | 7/2016 | Seitz |
| 2016/0270972 A1 | 9/2016 | Surushe |
| 2016/0324697 A1 | 11/2016 | Schoenbeck |
| 2017/0022339 A1 | 1/2017 | Hanschen et al. |
| 2017/0027775 A1 | 2/2017 | Barnes |
| 2017/0056256 A1 | 3/2017 | Smith |
| 2017/0071800 A1 | 3/2017 | Schonbeck |
| 2017/0079851 A1 | 3/2017 | Greening |
| 2017/0079854 A1 | 3/2017 | Butler |
| 2017/0087029 A1 | 3/2017 | Nelson |
| 2017/0142806 A1 | 5/2017 | Park |
| 2017/0252229 A1 | 9/2017 | Bonelli |
| 2017/0296399 A1 | 10/2017 | Kline et al. |
| 2017/0335498 A1 | 11/2017 | Hansen |
| 2018/0014979 A1 | 1/2018 | Fujita |
| 2018/0015709 A1 | 1/2018 | Takeuchi |
| 2018/0042777 A1 | 2/2018 | Dalal |
| 2018/0042784 A1 | 2/2018 | Koshijima |
| 2018/0042785 A1 | 2/2018 | Dalal |
| 2018/0042786 A1 | 2/2018 | Mueller |
| 2018/0271716 A1 | 9/2018 | Dalal |
| 2018/0271717 A1 | 9/2018 | Dria |
| 2018/0281296 A1 | 10/2018 | Uchida |
| 2019/0083323 A1 | 3/2019 | Sakai |
| 2019/0110936 A1 | 4/2019 | Becker |
| 2019/0125597 A1 | 5/2019 | Sauer et al. |
| 2020/0046576 A1 | 2/2020 | Schonbeck |
| 2020/0214363 A1 | 7/2020 | Sakai |
| 2020/0214904 A1 | 7/2020 | Tsunoda et al. |
| 2020/0397625 A1 | 12/2020 | Sakai |
| 2021/0000656 A1 | 1/2021 | Greening |
| 2021/0077315 A1 | 3/2021 | Schönbeck et al. |
| 2021/0077316 A1 | 3/2021 | Schönbeck et al. |
| 2021/0077317 A1 | 3/2021 | Schönbeck et al. |
| 2021/0085532 A1 | 3/2021 | Lenser et al. |
| 2021/0330514 A1 | 10/2021 | Lenser et al. |
| 2021/0393453 A1 | 12/2021 | Schönbeck et al. |
| 2022/0233362 A1 | 7/2022 | Lenser et al. |
| 2022/0287887 A1 | 9/2022 | Lenser et al. |

FOREIGN PATENT DOCUMENTS

| | | |
|---|---|---|
| CN | 104582945 A | 4/2015 |
| CN | 104703567 A | 6/2015 |
| CN | 104797228 A | 7/2015 |
| CN | 103434239 B | 11/2015 |
| CN | 204909840 U | 12/2015 |
| CN | 104837455 B | 4/2018 |
| CN | 108601686 A | 9/2018 |
| EP | 0666308 A2 | 8/1995 |
| EP | 1256594 A1 | 11/2002 |
| EP | 1447066 A1 | 8/2004 |
| EP | 2100575 A2 | 9/2009 |
| EP | 1263580 B1 | 9/2010 |
| EP | 1990188 B1 | 10/2012 |
| EP | 2891480 A1 | 7/2015 |
| EP | 2841364 B1 | 8/2016 |
| EP | 3170884 A1 | 5/2017 |
| EP | 3246443 A1 | 11/2017 |
| EP | 2647360 B1 | 6/2018 |
| EP | 3251642 B1 | 8/2020 |
| JP | 2004223238 A | 8/2004 |
| JP | 2007521036 A | 8/2007 |
| JP | 2011139843 A | 7/2011 |
| JP | 4934835 B2 | 3/2012 |
| JP | 5036641 B2 | 7/2012 |
| JP | 2012524645 A | 10/2012 |
| JP | 2017064233 A | 4/2017 |
| JP | 2017065142 A | 4/2017 |
| JP | 6240733 B1 | 11/2017 |

(56) References Cited

FOREIGN PATENT DOCUMENTS

| | | |
|---|---|---|
| WO | 9115365 A1 | 10/1991 |
| WO | 9510996 A1 | 4/1995 |
| WO | 95010996 A1 | 4/1995 |
| WO | 9511652 A1 | 5/1995 |
| WO | 9516746 A1 | 6/1995 |
| WO | 9828123 A1 | 7/1998 |
| WO | 9919449 A1 | 4/1999 |
| WO | 2000045763 A1 | 8/2000 |
| WO | 2000059430 A1 | 10/2000 |
| WO | 0073031 A1 | 12/2000 |
| WO | 02067809 A2 | 9/2002 |
| WO | 2003007864 A1 | 1/2003 |
| WO | 2004017882 A2 | 3/2004 |
| WO | 2004017885 A1 | 3/2004 |
| WO | 2004041990 A1 | 5/2004 |
| WO | 2004060652 A1 | 7/2004 |
| WO | 2006020690 A1 | 2/2006 |
| WO | 2006124337 A1 | 11/2006 |
| WO | 2006138725 A2 | 12/2006 |
| WO | 2007036907 A3 | 4/2007 |
| WO | 2008023291 A3 | 2/2008 |
| WO | 2008156075 A1 | 12/2008 |
| WO | 2009082277 A1 | 7/2009 |
| WO | 2009146307 A1 | 12/2009 |
| WO | 2010055699 A1 | 5/2010 |
| WO | 2010118214 A1 | 10/2010 |
| WO | 2010126415 A1 | 11/2010 |
| WO | 2011080643 A2 | 7/2011 |
| WO | 2011125893 A1 | 10/2011 |
| WO | 2012030571 A2 | 3/2012 |
| WO | 2012052172 A1 | 4/2012 |
| WO | 2012112501 A1 | 8/2012 |
| WO | 2012137553 A1 | 10/2012 |
| WO | 2012154318 A1 | 11/2012 |
| WO | 2013018846 A1 | 2/2013 |
| WO | 2013027390 A1 | 2/2013 |
| WO | 2013047890 A1 | 4/2013 |
| WO | 2013132403 A1 | 9/2013 |
| WO | 2013157365 A1 | 10/2013 |
| WO | 2013163141 A1 | 10/2013 |
| WO | 2014011839 A1 | 1/2014 |
| WO | 2015168032 A1 | 11/2015 |
| WO | 2015195467 A1 | 12/2015 |
| WO | 2015195468 A1 | 12/2015 |
| WO | 2016069269 A1 | 5/2016 |
| WO | 2016073713 A1 | 5/2016 |
| WO | 2016109514 A1 | 7/2016 |
| WO | 2018031841 A1 | 2/2018 |
| WO | 2018183315 A1 | 10/2018 |
| WO | 2016121979 A1 | 1/2019 |
| WO | 2019089689 A2 | 5/2019 |

OTHER PUBLICATIONS

All Office Actions; U.S. Appl. No. 15/674,563, filed Aug. 11, 2017.
All Office Actions; U.S. Appl. No. 15/674,575, filed Aug. 11, 2017.
All Office Actions; U.S. Appl. No. 15/674,596, filed Aug. 11, 2017.
All Office Actions; U.S. Appl. No. 15/674,625, filed Aug. 11, 2017.
All Office Actions; U.S. Appl. No. 16/049,977, filed Jul. 31, 2018.
All Office Actions; U.S. Appl. No. 16/740,814, filed Jan. 13, 2020.
All Office Actions; U.S. Appl. No. 16/741,819, filed Jan. 14, 2020.
All Office Actions; U.S. Appl. No. 16/748,885, filed Jan. 22, 2020.
All Office Actions; U.S. Appl. No. 17/110,351, filed Dec. 3, 2020.
All Office Actions; U.S. Appl. No. 17/195,677, filed Mar. 9, 2021.
All Office Actions; U.S. Appl. No. 17/195,679, filed Mar. 9, 2021.
All Office Actions; U.S. Appl. No. 17/350,240, filed Jun. 17, 2021.
All Office Actions; U.S. Appl. No. 17/368,021, filed Jul. 6, 2021.
All Office Actions; U.S. Appl. No. 17/720,363, filed Apr. 14, 2022.
All Office Actions; U.S. Appl. No. 17/830,452, filed Jun. 2, 2022.
All Office Actions; U.S. Appl. No. 18/191,334, filed Mar. 28, 2023.
U.S. Appl. No. 18/191,334, filed Mar. 28, 2023 to Todd Douglas Lenser et al.
All Office Actions; U.S. Appl. No. 18/485,494, filed Oct. 12, 2023.
U.S. Appl. No. 18/485,494, filed Oct. 12, 2023, to Todd Douglas Lenser ,et. al.

* cited by examiner

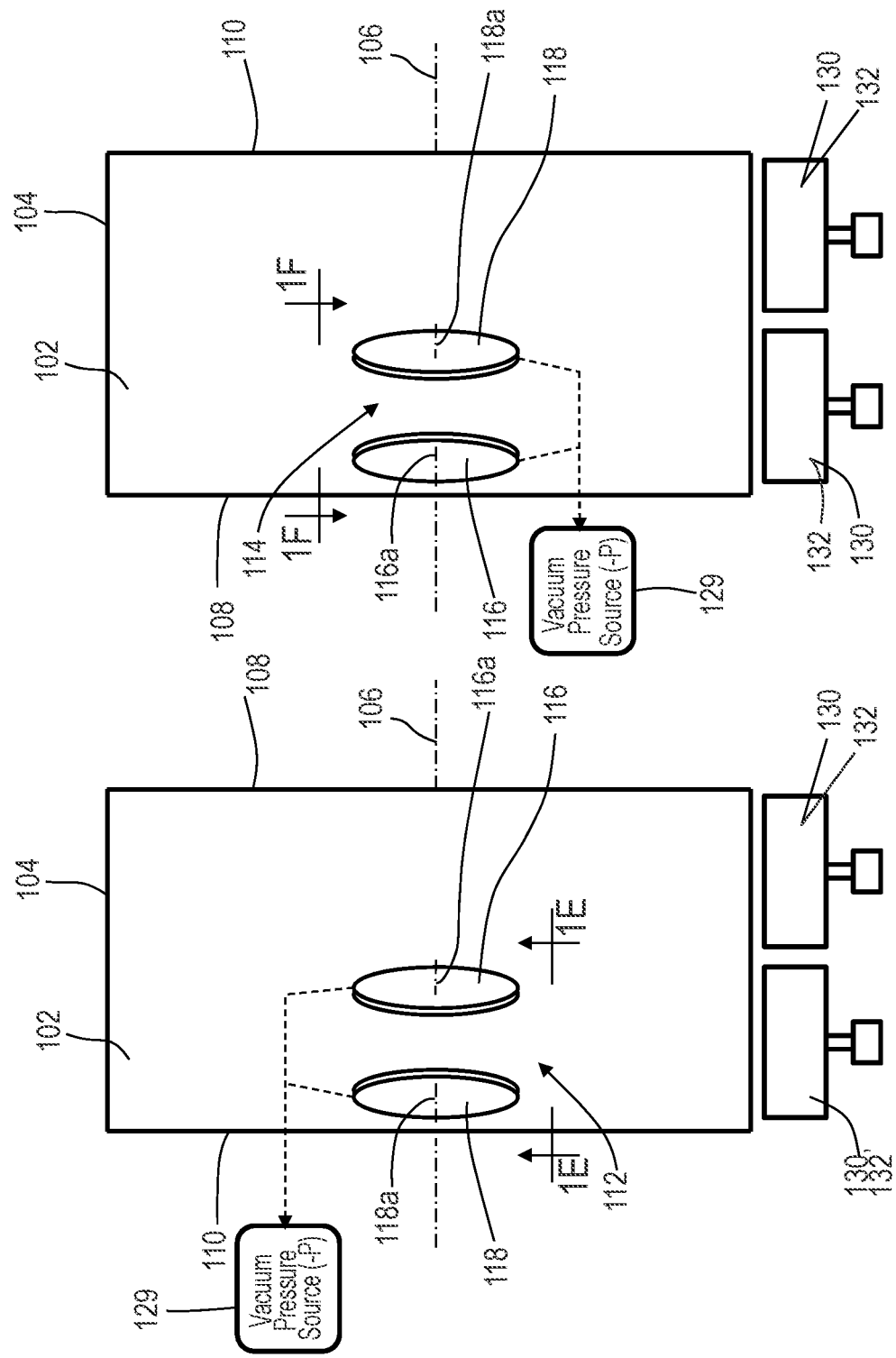

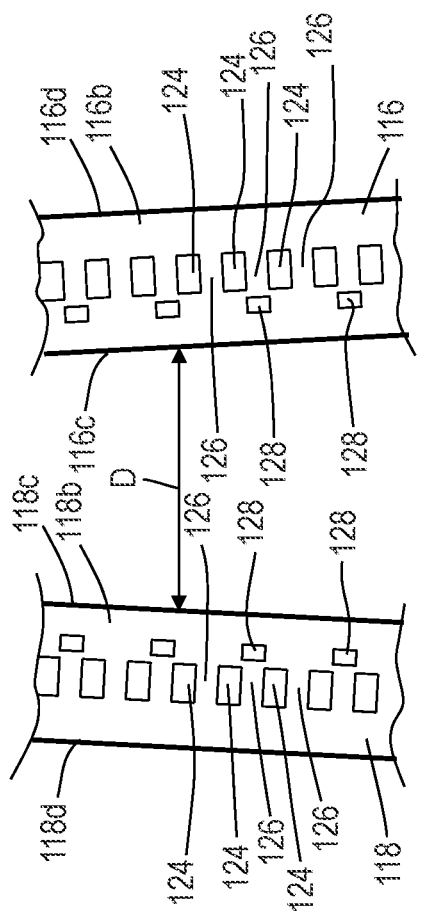
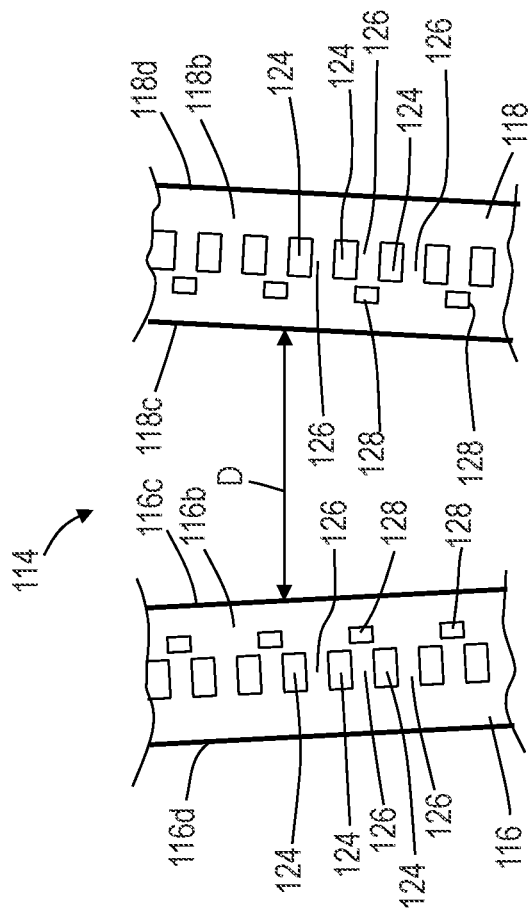
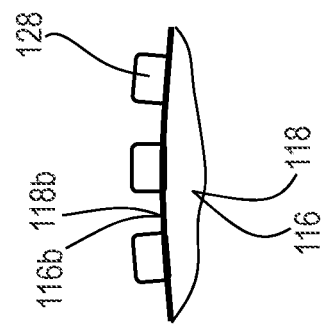

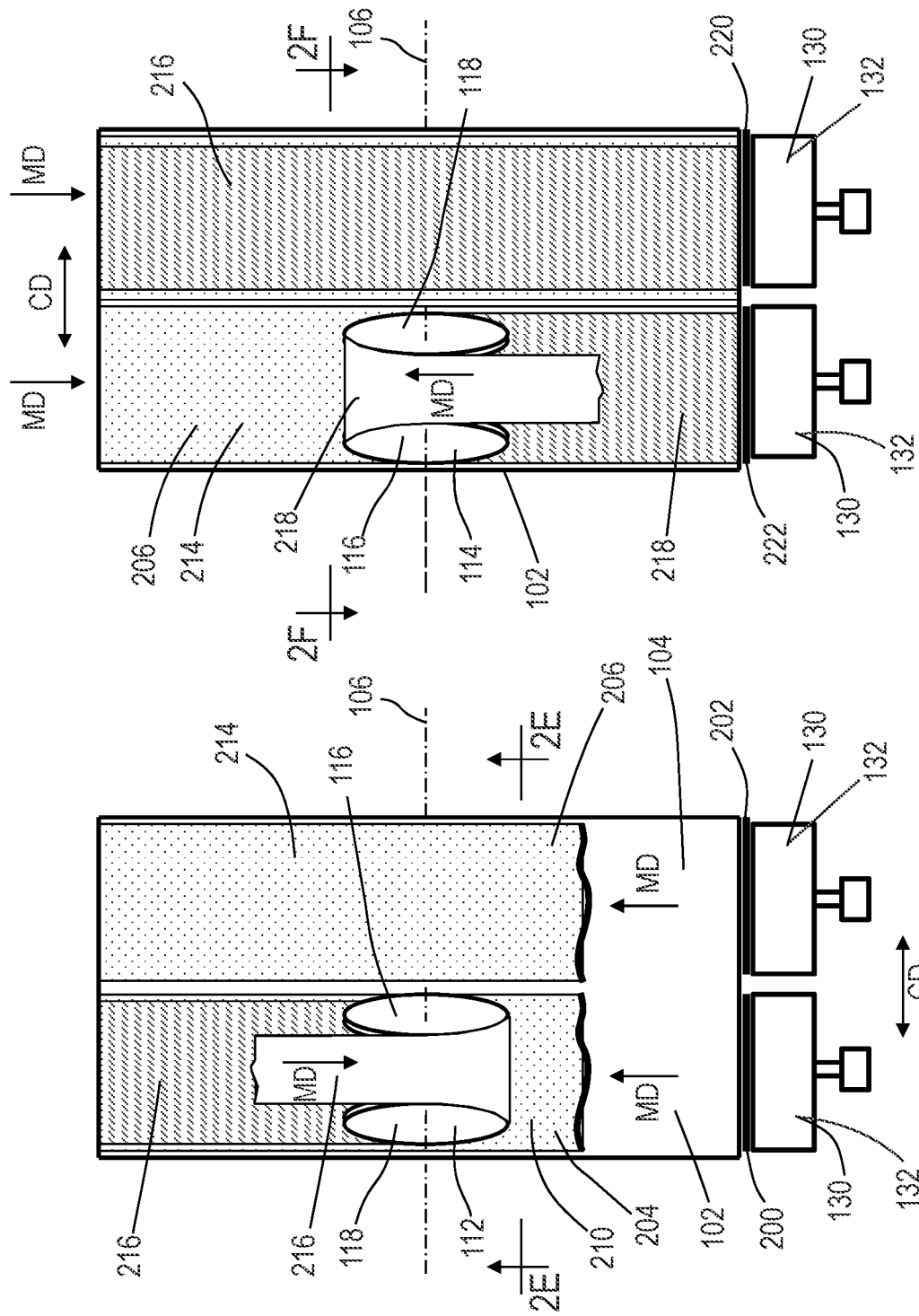

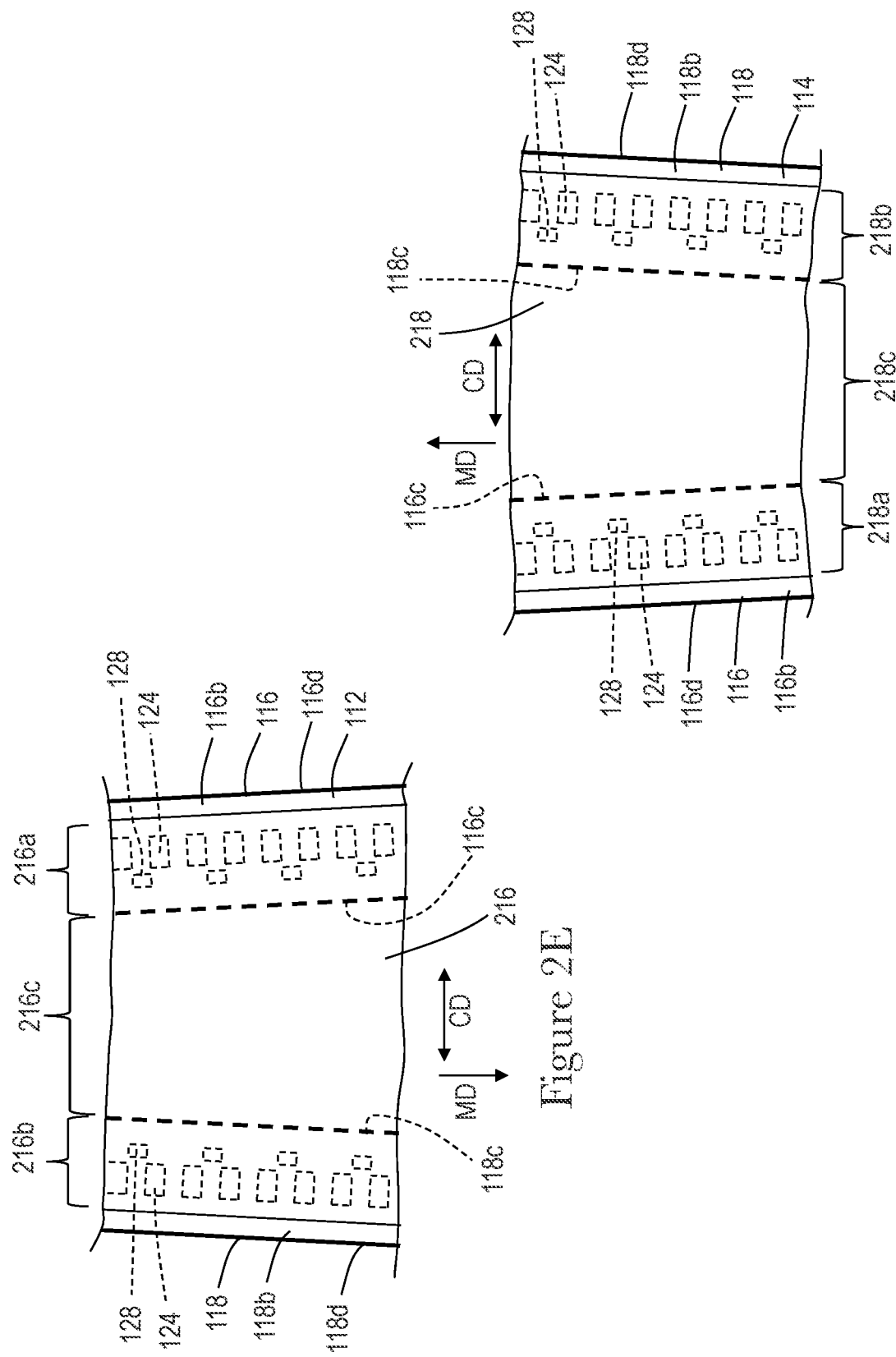

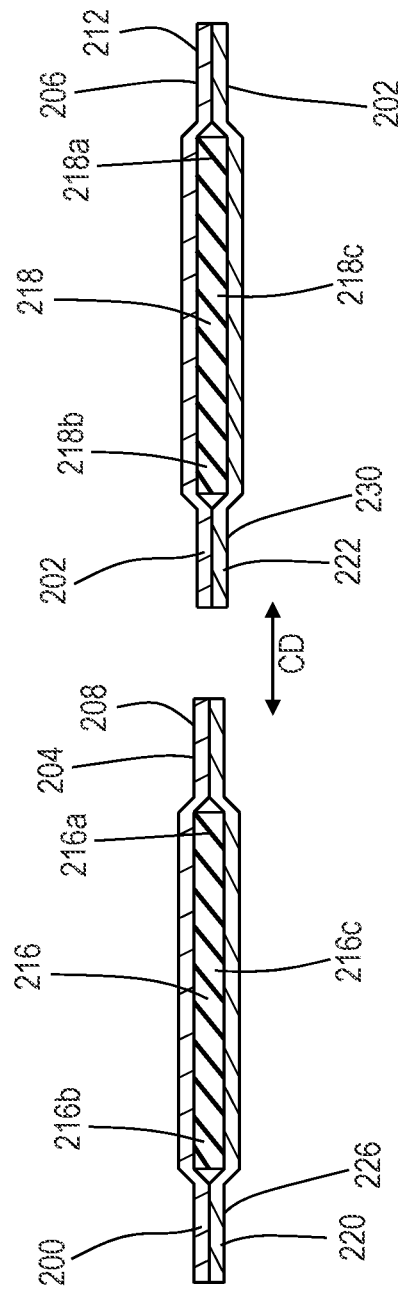
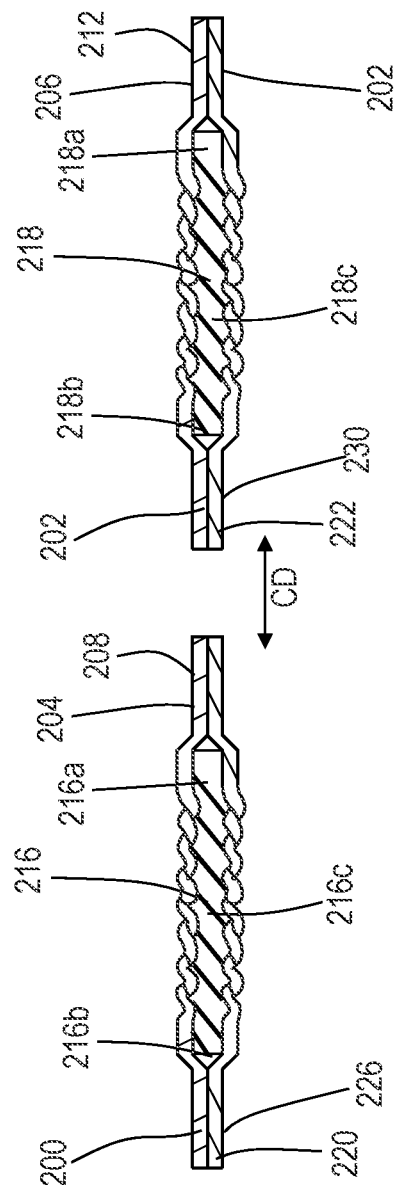
Figure 2G
Figure 2H

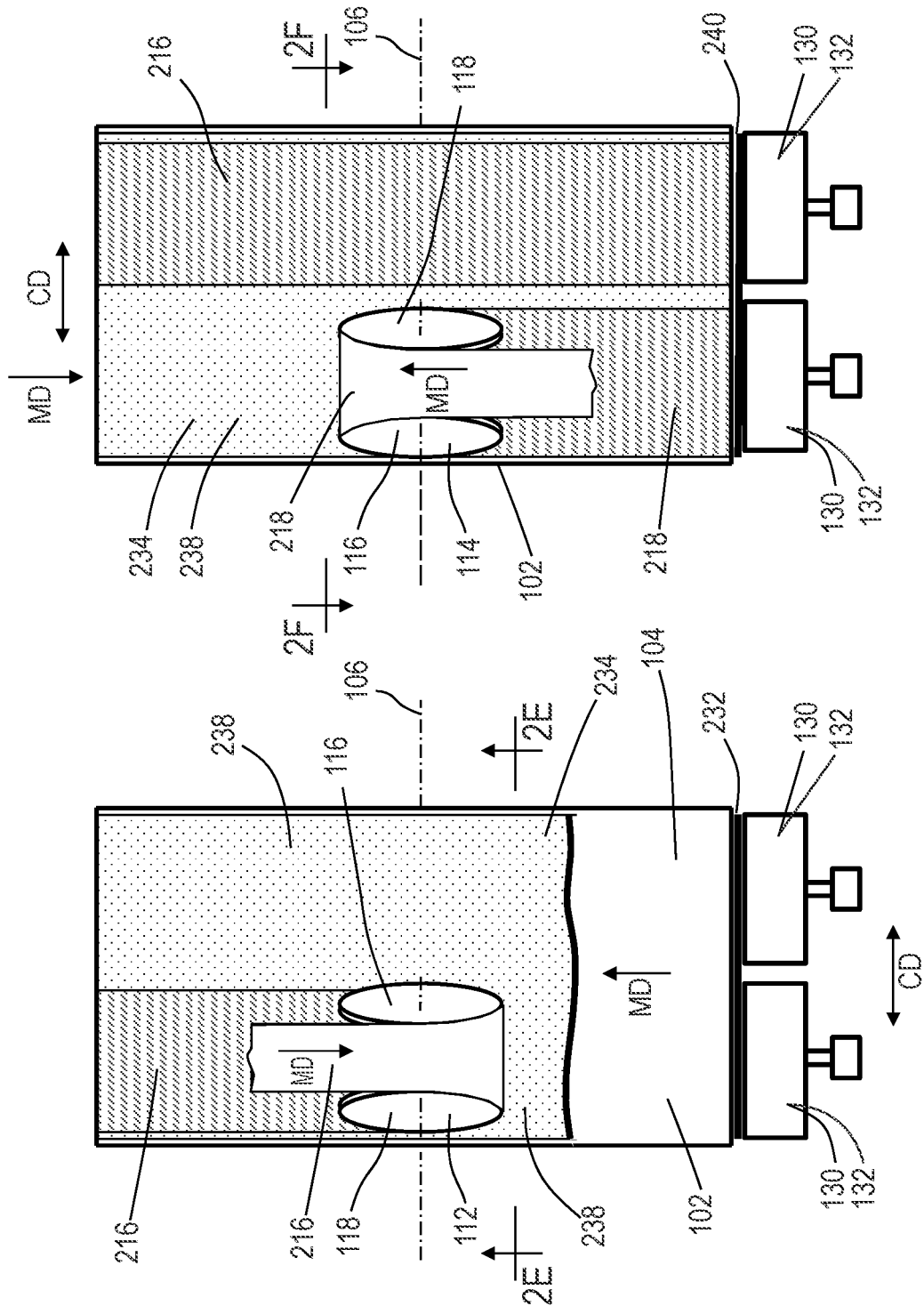

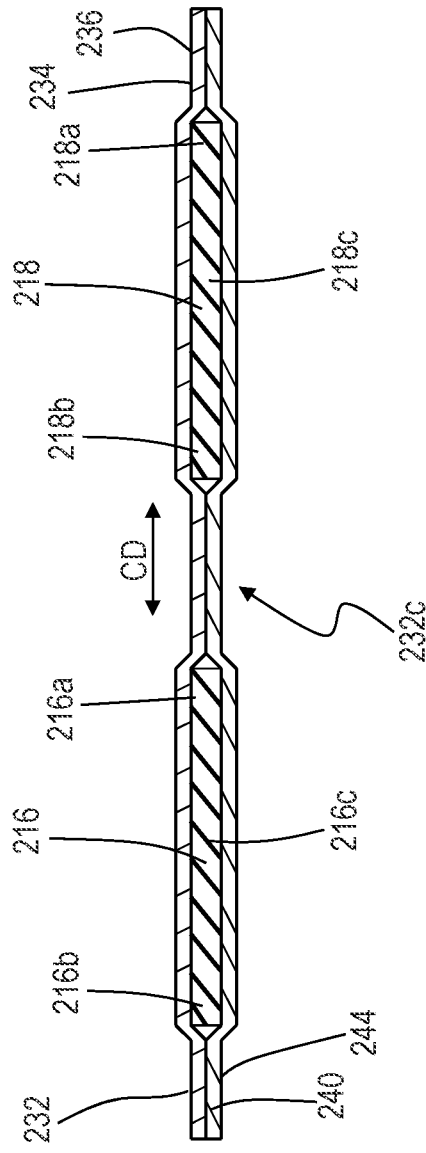
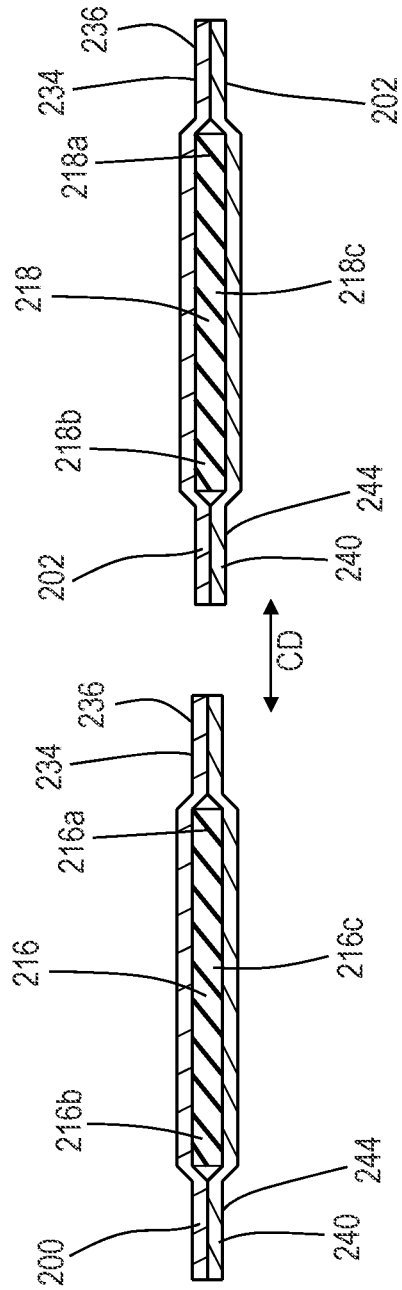
Figure 3E
Figure 3F

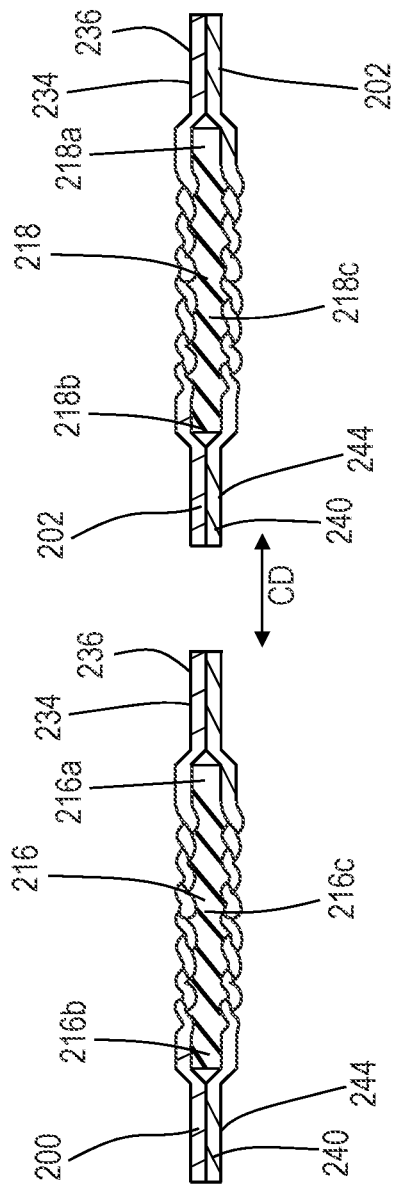
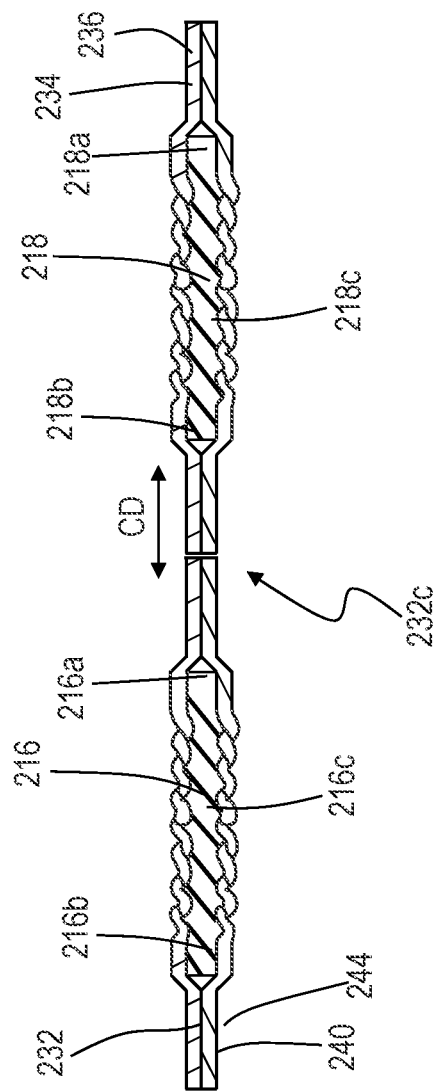
Figure 3G
Figure 3H

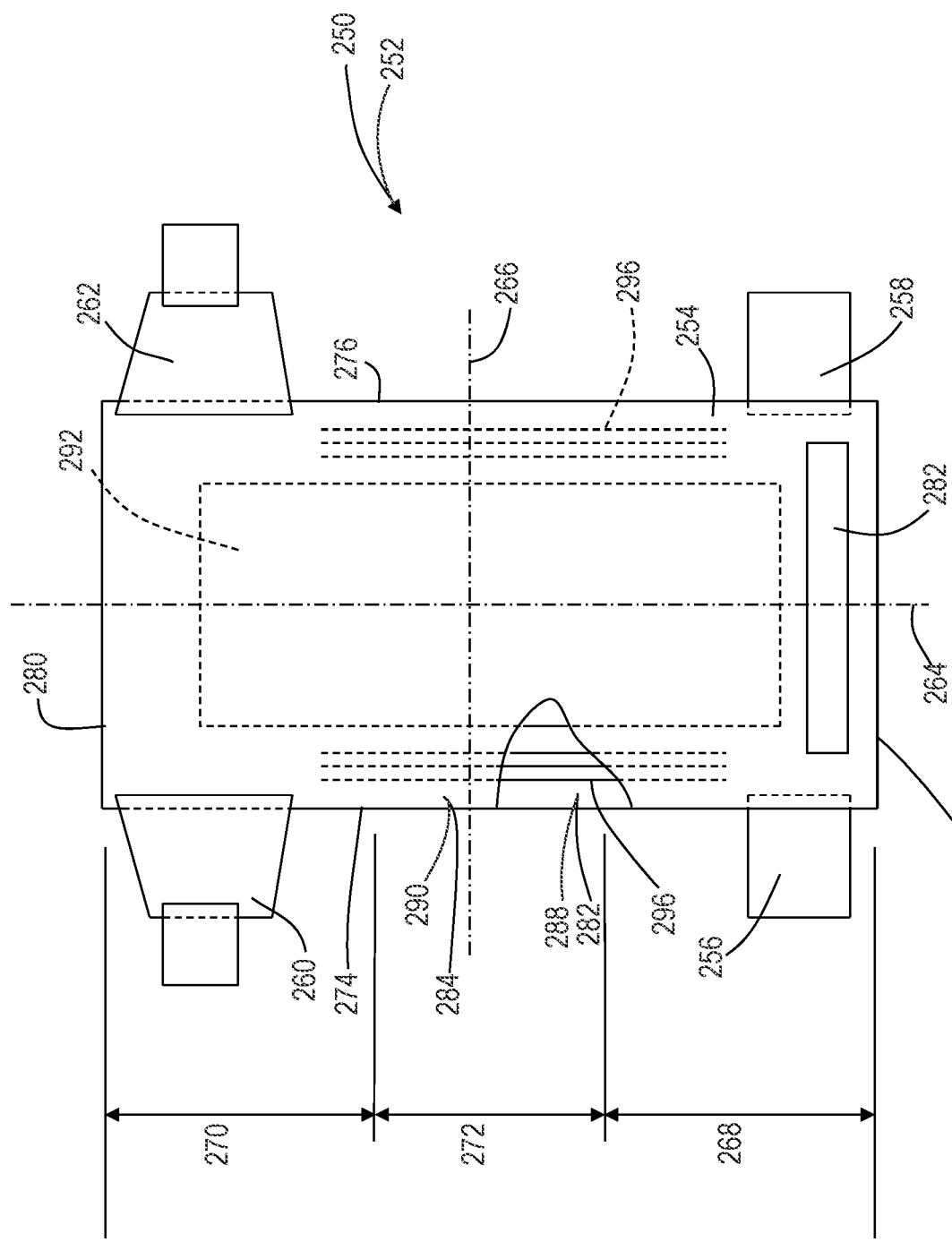

METHOD AND APPARATUS FOR ASSEMBLING ABSORBENT ARTICLES

CROSS REFERENCE TO RELATED APPLICATIONS

This application is a continuation of U.S. patent application Ser. No. 17/830,452, filed on Jun. 2, 2022, which is a continuation of U.S. patent application Ser. No. 17/350,240, filed on Jun. 17, 2021, now issued U.S. Pat. No. 11,328,798 on Jul. 12, 2022, which is a continuation of U.S. patent application Ser. No. 16/740,814, filed on Jan. 13, 2020, now issued as U.S. Pat. No. 11,071,654, on Jul. 27, 2021, which is a continuation of U.S. patent application Ser. No. 15/674,563, filed on Aug. 11, 2017, now issued as U.S. Pat. No. 10,568,775, on Feb. 25, 2020, which claims the benefit of U.S. Provisional Application Nos. 62/374,010, filed on Aug. 12, 2016; 62/406,025, filed on Oct. 10, 2016; and 62/419,515, filed on Nov. 9, 2016, the entireties of which are all fully incorporated by reference herein.

FIELD OF THE INVENTION

The present disclosure relates to methods for manufacturing absorbent articles, and more particularly, to apparatuses and methods for assembling elastic laminates for making absorbent article components.

BACKGROUND OF THE INVENTION

Along an assembly line, various types of articles, such as for example, diapers and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from advancing web or webs are combined with other individual components created from other advancing web or webs. Webs of material and component parts used to manufacture diapers may include: backsheets, topsheets, leg cuffs, waist bands, absorbent core components, front and/or back ears, and fastening components. Once the desired component parts are assembled, the advancing web(s) and component parts are subjected to a final knife cut to separate the web(s) into discrete diapers or other absorbent articles.

Some diaper components, such as leg elastics, barrier leg cuff elastics, stretch side panels, and waist elastics, are constructed from elastic laminates. Such elastic laminates may be assembled in various ways depending on the particular diaper design. For example, some elastic laminates may be constructed from one or more nonwoven substrates bonded to an elastic film. In some configurations, the elastic film may be stretched and then bonded with the nonwoven substrates to form an elastic laminate.

Some existing elastic laminate assembly operations may have certain drawbacks. For example, manufacturing operations may be configured with machines adapted to grip and stretch the films before bonding. However, while gripping the films during the stretching operation, the machines may tear or pierce the films. In addition, with some gripping operations, relatively large portions of the film may remain unstretched in the assembled elastic laminate. As such, the unstretched and/or damaged portions of the film may add no benefit with respect to the desired elasticity of the assembled elastic laminate, and thus, may represent wasted material and expense. In some assembly operations, the elastic laminate may be slit through both the film and nonwovens along the machine direction into two lanes, wherein each lane of elastic laminate may then be combined with additional components and/or substrates, and subsequently converted into discrete diaper components. However, the slit edge of the elastic laminate having exposed elastic film may detract from the aesthetics of the final component assembly incorporating the slit laminate.

Consequently, it would be beneficial to provide methods and apparatuses for assembling elastic laminates that are configured to minimize damaged and/or unstretched portions of films incorporated therein, and may also be configured to eliminate the need to slit the laminate through the film to help maximize the aesthetic appearance of the laminate when placed in an assembled product.

SUMMARY OF THE INVENTION

The present disclosure relates to assembling elastic laminates that may be used to make absorbent article components. Aspects of the apparatus and method involve an anvil adapted to rotate about an axis of rotation, wherein first and second spreader mechanisms adjacent the anvil roll are axially and angularly displaced from each other with respect to the axis of rotation. During the assembly process, at least one substrate, such as a nonwoven, may be advanced in a machine direction onto the rotating anvil. The first spreader mechanism operates to stretch a first elastic material in the cross direction, and the second spreader mechanism operates to stretch a second elastic material in the cross direction. In some configurations, the first and/or second elastic materials may be elastic films and/or elastic laminates. The stretched first and second elastic materials advance from the spreader mechanisms and onto the at least one substrate on the anvil roll. The combined at least one substrate and elastic materials may then be ultrasonically bonded together on the anvil to form at least one elastic laminate.

In one form, a method for assembling elastic laminates comprises the steps of: providing a first substrate a comprising a first surface and an opposing second surface, and defining a width in a cross direction; wrapping the first surface of the first substrate onto an outer circumferential surface of an anvil; providing a first elastic material and a second elastic material, the first elastic material and the second elastic material each comprising a first edge region and a second edge region separated from the first edge region in the cross direction by a central region; stretching the central region of the first elastic material in the cross direction; and stretching the central region of the second elastic material in the cross direction. The method may include advancing the first elastic material onto the anvil at a first application zone, wherein the stretched central region of the first elastic material is positioned in contact with the second surface of the first substrate; and advancing the second elastic material onto the anvil at a second application zone downstream of the first application zone, wherein the stretched central region of the second elastic material is positioned in contact with the second surface of the first substrate, and wherein the second elastic material is separated from the first elastic material in a cross direction. The stretched central regions of the first and second elastic materials may be ultrasonically bonded with the first substrate, forming an elastic laminate. The elastic laminate may be cut in the machine direction into a first elastic laminate and a second elastic laminate.

In another form, a method for assembling elastic laminates comprises the steps of: providing a first substrate a comprising a first surface and an opposing second surface, and defining a width in a cross direction; wrapping the first surface of the first substrate onto an outer circumferential surface of an anvil; providing a first elastic material and a second elastic material, the first elastic material and the second elastic material each comprising a first edge region and a second edge region separated from the first edge region in the cross direction by a central region; stretching the central region of the first elastic material in the cross direction; and stretching the central region of the second elastic material in the cross direction. The method may include advancing the first elastic material onto the anvil, wherein the stretched central region of the first elastic material is positioned in contact with the second surface of the first substrate; and advancing the second elastic material onto the anvil, wherein the stretched central region of the second elastic material is positioned in contact with the second surface of the first substrate, and wherein the second elastic material is separated from the first elastic material in a cross direction. The stretched central regions of the first and second elastic materials may be ultrasonically bonded with the first substrate to form an elastic laminate, and the elastic laminate may be cut along the machine direction into a first elastic laminate and a second elastic laminate.

In yet another form, a method for assembling elastic laminates comprises the steps of: advancing a first substrate in a machine direction onto a rotating anvil; providing a first elastic material and a second elastic material, the first elastic material and the second elastic material each comprising a first edge region and a second edge region separated from the first edge region in the cross direction by a central region; and providing a first spreader mechanism and a second spreader mechanism, the first and second spreader mechanisms each comprising a first disk and a second disk canted relative each other, each disk comprising an outer rim, wherein as the first and second disks rotate, the outer rims are separated from each other by a distance that increases from a minimum distance at a first location to a maximum distance at a second location. The method further includes advancing the first elastic material onto the first spreader mechanism at or downstream of the first location; stretching the central region of the first elastic material in the cross direction by rotating the first disk and the second disk of the first spreader mechanism; removing the first elastic material from the first spreader mechanism at or upstream of the second location; and transferring the first elastic material from the first spreader mechanism onto the first substrate on the anvil at a first application zone. The method may also include advancing the second elastic material onto the second spreader mechanism at or downstream of the first location; stretching the central region of the second elastic material in the cross direction by rotating the first disk and the second disk of the second spreader mechanism; removing the second elastic material from the second spreader mechanism at or upstream of the second location; and transferring the second elastic material from the second spreader mechanism onto the first substrate on the anvil at a second application zone.

BRIEF DESCRIPTION OF THE DRAWINGS

FIG. 1C is a left side view of the apparatus from FIG. 1B taken along line 1C-1C.

FIG. 1D is a right side view of the apparatus from FIG. 1B taken along line 1D-1D.

FIG. 1E is a detailed view of a first spreader mechanism from FIG. 1C taken along line 1E-1E.

FIG. 1F is a detailed view of a second spreader mechanism from FIG. 1D taken along line 1F-1F.

FIG. 1G is a detailed view of radially protruding nubs on an outer rim of a disk.

FIG. 1HB is a detailed view of the anvil from FIG. 1HA taken along line 1HB-1HB.

FIG. 2B is a left side view of the apparatus from FIG. 2A taken along line 2B-2B.

FIG. 2C is a right side view of the apparatus from FIG. 2A taken along line 2C-2C.

FIG. 2E is a detailed view of a first elastic material advancing on a first spreader mechanism from FIGS. 2B and 3B taken along line 2E-2E.

FIG. 2F is a detailed view of a second elastic material advancing on a second spreader mechanism from FIGS. 2C and 3C taken along line 2F-2F.

FIG. 2G is a cross sectional view of the first elastic laminate and the second elastic laminate from FIG. 2A taken along line 2G-2G.

FIG. 2H is a cross-sectional view of the first elastic laminate and the second elastic laminate from FIG. 2G in a relaxed, contracted condition.

FIG. 3B is a left side view of the apparatus from FIG. 3A taken along line 3B-3B.

FIG. 3C is a right side view of the apparatus from FIG. 3A taken along line 3C-3C.

FIG. 3E is a cross sectional view of an elastic laminate from FIG. 3A taken along line 3E-3E.

FIG. 3F is a cross sectional view of the first elastic laminate and the second elastic laminate from FIG. 3A taken along line 3F-3F.

FIG. 3G is a cross-sectional view of the first elastic laminate and the second elastic laminate from FIG. 3F in a relaxed, contracted condition.

FIG. 3H is a cross-sectional view of the elastic laminate from FIG. 3E in a relaxed, contracted condition.

FIG. 4A is a partially cut away plan view of an absorbent article in the form of a taped diaper that may include one or more elastic laminates manipulated during manufacture according to the apparatuses and methods disclosed herein with the portion of the diaper that faces away from a wearer oriented towards the viewer.

DETAILED DESCRIPTION OF THE INVENTION

Figure 1A:
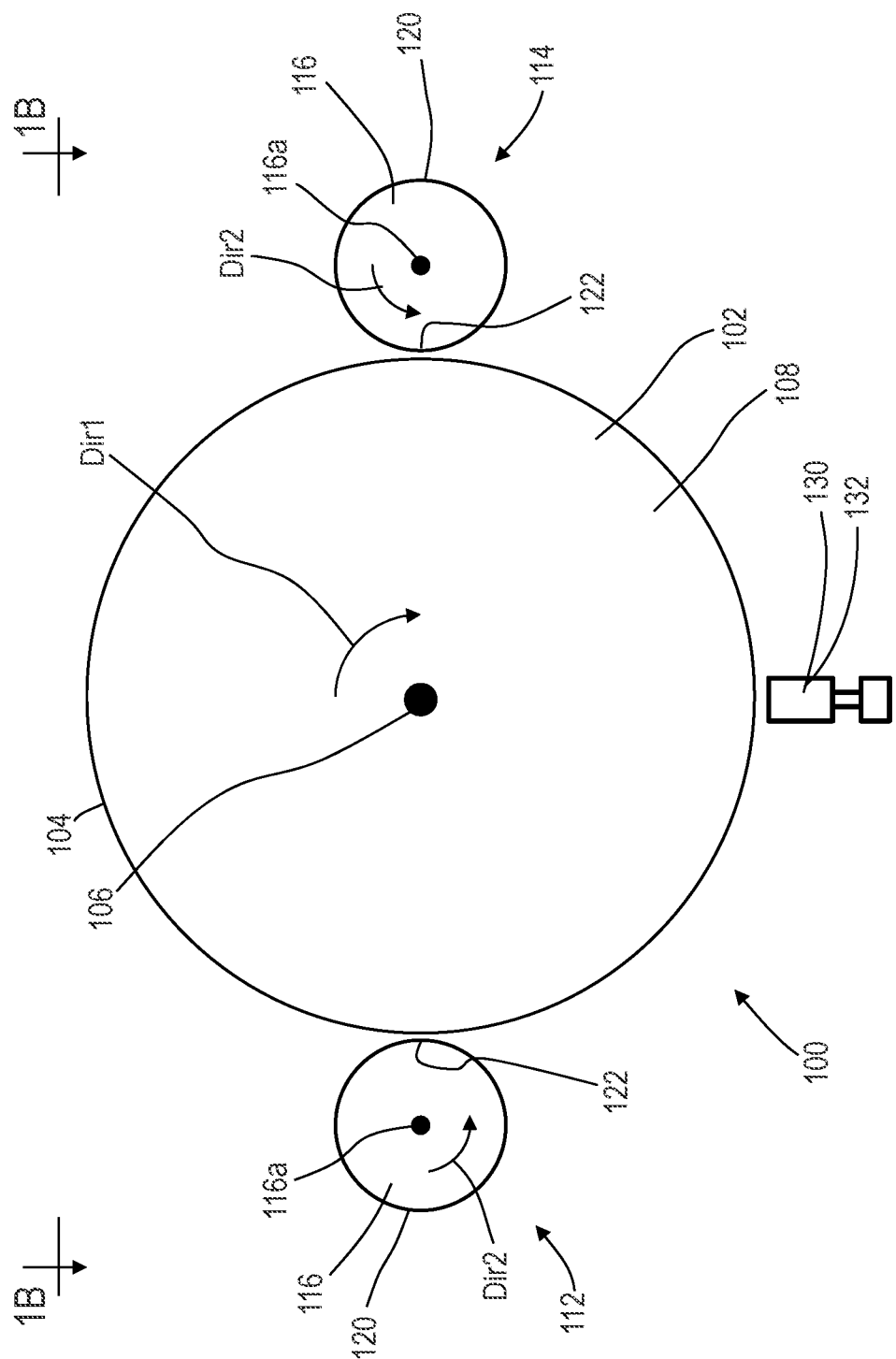
FIG. 1A is a schematic side view of an apparatus for assembling an elastic laminate.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The present disclosure relates to apparatuses and methods for manufacturing absorbent articles, and more particularly, apparatuses and methods for assembling elastic laminates that may be used to make absorbent article components. Particular aspects of the present disclosure involve an anvil adapted to rotate about an axis of rotation. First and second spreader mechanisms adjacent the anvil roll are axially and angularly displaced from each other with respect to the axis of rotation. During the assembly process, at least first and second substrates may be advanced in a machine direction onto the rotating anvil, wherein the substrates are separated from each other in a cross direction. In some configurations, the substrates may be nonwovens. The first spreader mechanism operates to stretch a first elastic material in the cross direction, and the second spreader mechanism operates to stretch a second elastic material in the cross direction. In some configurations, the first and/or second elastic materials may be elastic films and/or elastic laminates. The stretched first and second elastic materials advance from the spreader mechanisms and onto respective first and second substrates on the anvil roll. The combined substrates and elastic materials are then ultrasonically bonded together on the anvil to form first and second elastic laminates. In some configurations, a single elastic laminate may be assembled on the anvil and subsequently slit into two or more separate elastic laminates. For example, a first substrate may be advanced in a machine direction onto the rotating anvil, and stretched first and second elastic materials advance from the spreader mechanisms onto the first substrate on the anvil roll. A second substrate is combined with the first substrate, first elastic material, and second elastic material and ultrasonically bonded together to form an elastic laminate. The elastic laminate is then separated along the machine direction in a central region between the first and second elastic materials to form first and second elastic laminates. The first and second elastic laminates may then advance from the anvil and may be subject to subsequent manufacturing operations and converted into absorbent article components.

As discussed below in more detail, the spreader mechanism configurations help to minimize damaged and/or unstretched portions of elastic materials incorporated into the elastic laminates. In some configurations, the relative placement of the spreader mechanisms help to enable the assembly of more than one elastic laminate on a single anvil, and thus, may eliminate the need to create more than one elastic laminate by subsequently slitting an assembled elastic laminate. In other configurations, the relative placement of the spreader mechanisms help to enable the assembly of one elastic laminate on a single anvil that is subsequently slit into more than one elastic laminate without having to cut through both the elastic materials and substrates.

It is to be appreciated that aspects of the methods and apparatuses herein may be configured in various ways. To help provide additional context to a subsequent discussion of the method configurations, the following provides a description of apparatuses that may be configured to operate in accordance with the methods disclosed herein.

Figure 1B:
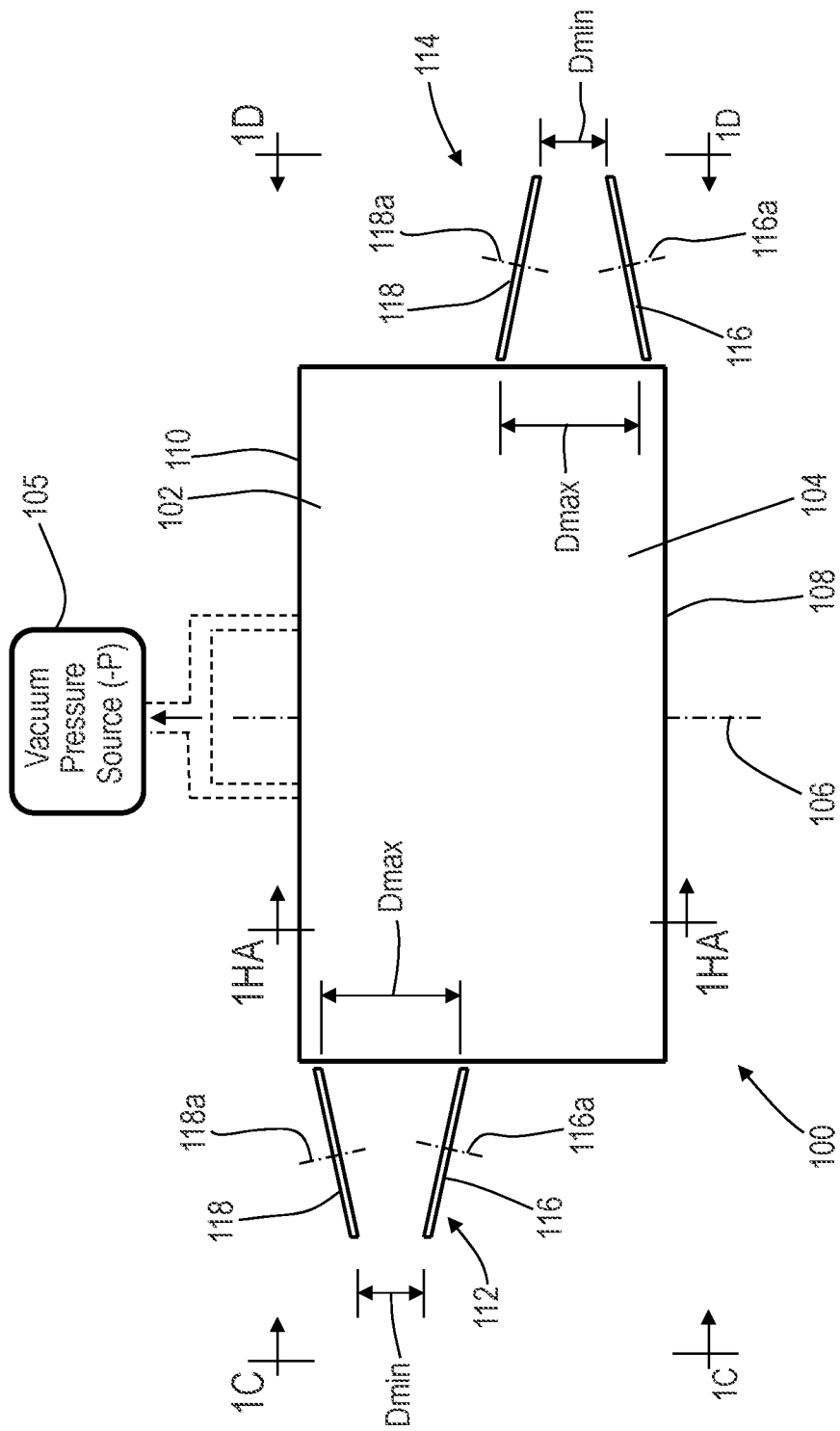
FIG. 1B is a top side view of the apparatus from FIG. 1A taken along line 1B-1B.

FIGS. 1A-1D show schematic side views of an apparatus 100 configured to assemble elastic laminates. As shown in FIGS. 1A-1D, the apparatus includes an anvil 102 having a cylindrically-shaped outer circumferential surface 104 and adapted to rotate in a first direction Dir1 about a first axis of rotation 106. Although the first direction Dir1 is depicted in FIG. 1A as clockwise, it is to be appreciated that the anvil 100 may be configured to rotate such that the first direction Dir1 is counterclockwise. The anvil roll 100 may extend axially for a length between a first end 108 and a second end 110. As discussed in more detail below, substrates and elastic materials may be combined on the rotating anvil 102 to form at least two elastic laminates. It is to be appreciated that the substrates and elastic materials may be configured in various ways. For example, the substrates may be configured as nonwovens, and the elastic materials may be configured as elastic films and/or elastic laminates. As shown in FIG. 1B, the anvil 102, and more particularly, the outer circumferential surface 104 may also be fluidly connected with a vacuum pressure source 105. As such, vacuum air pressure may be used to help hold the substrates and elastic materials onto the outer circumferential surface 104 of the anvil 102 during operation.

With continued reference to FIGS. 1A-1D, the apparatus 100 may also include a first spreader mechanism 112 and a second spread mechanism 114. As discussed in more detail below, the first and second spreader mechanisms 112, 114 operate to stretch elastic materials during the elastic laminate assembly process, and the stretched elastic materials are advanced from the spreader mechanisms 112, 114 onto substrates on the rotating anvil 102. As shown in FIG. 1A, the first spreader mechanism 112 is angularly displaced from the second spreader mechanism 114 with respect to the first axis of rotation 106. It is to be appreciated that the apparatus 100 may be configured with various different angular displacements between the first spreader mechanism 112 and the second spreader mechanism 114. As shown in FIG. 1B, the first spreader mechanism 112 is also axially displaced from the second spreader mechanism 114 along the first axis of rotation 106.

As shown in FIGS. 1A-1F, each spreader mechanism 112, 114 includes a first disk 116 and a second disk 118, wherein the first disk 116 is displaced from the second disk 118 along the axis of rotation 106. The first disk 116 is adapted to rotate about an axis of rotation 116a and the second disk 118 is adapted to rotate about an axis of rotation 118a, wherein the first and second disks 116, 118 rotate in a second direction Dir2 that is opposite the first direction Dir1. Although the second direction Dir2 is depicted in FIG. 1A as counterclockwise, it is to be appreciated that the disks 116, 118 may be configured to rotate such that the second direction Dir2 is clockwise. In addition, the first disk 116 includes an outer rim 116b extending axially between an inner edge 116c and an outer edge 116d, and the second disk 118 includes an outer rim 118b extending axially between an inner edge 118c and an outer edge 118d.

As shown in FIGS. 1A, 1B, 1E, and 1F, the first disk 116 and the second disk 118 are canted relative to each other such that the outer rims 116b, 118b are separated from each other by a distance D that increases from a minimum distance Dmin at a first location 120 to a maximum distance Dmax at a second location 122. As discussed below, elastic materials, such as elastic films, are advanced in a machine direction MD onto the outer rims 116b, 118b during operation. Because the first and second disks 116, 118 are canted, rotation of the disks 116, 118 causes the rims 116b, 118b to pull on edges regions of elastic materials and stretch the elastic materials in a cross direction CD before the elastic materials advance onto the anvil 102. As such, the disks 116, 118 may also be configured to help grip opposing edge regions of the elastic material during operation. For example, with particular reference to FIGS. 1E and 1F, the first disk 116 and the second disk 118 may each include a channel 124 extending radially inward from the rims 116b, 118b. In turn, the channels 124 may be fluidly connected with a vacuum pressure source 129. As such, vacuum air pressure may be used to help hold the elastic materials onto the rims 116b, 118b during operation. The disks 116, 118 may also include support members 126 extending across the channels 124 to the help prevent the elastic materials from being drawn into the channels 124 by the vacuum air pressure. As shown in FIGS. 1E, 1F, and 1G, the disks 116, 118 may also include nubs 128 that protrude radially outward from the rims 116b, 118b. As such, the nubs 128 may also act to help prevent the edge regions of the elastic materials from sliding along the rims 116b, 118b while stretching the elastic materials. It is to be appreciated that additional nubs 128 may be positioned inboard or outboard of the channels 124. In addition, nubs 128 may also be positioned on the support members 126.

Figure 1H:
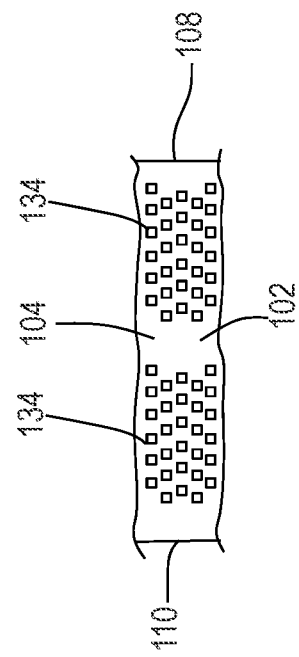
FIG. 1HA is a detailed view of an anvil from FIG. 1B taken along line 1HA-1HA.
Figure 1H:
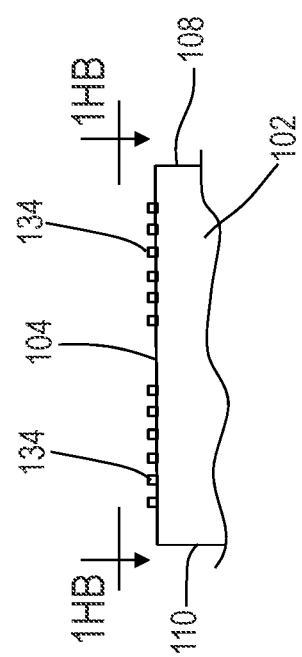

As mentioned above, stretched elastic materials and substrates are combined on the anvil 102. The combined substrates and elastic materials may then be ultrasonically bonded together on the anvil 102 to form elastic laminates. As shown in FIGS. 1A, 1C, and 1D, the apparatus 100 may include one or more ultrasonic mechanisms 130 adjacent the anvil 102. It is to be appreciated that the ultrasonic mechanism 130 may include a horn 132 and may be configured to impart ultrasonic energy to the combined substrates and elastic materials on the anvil 102. As shown in FIGS. 1HA and 1HB, the anvil roll 102 may include a plurality of pattern elements 134 extending radially outward from the outer circumferential surface 104 of the anvil 102. As such, the ultrasonic mechanism may apply energy to the horn 132 to create resonance of the horn at frequencies and amplitudes so the horn 132 vibrates rapidly in a direction generally perpendicular to the substrates and elastic materials being advanced past the horn 132 on the rotating anvil 102. Vibration of the horn 132 generates heat to melt and bond the substrates and elastic material together in areas supported by the pattern elements 134 on the anvil 102. It is to be appreciated that aspects of the ultrasonic mechanisms may be configured in various ways, such as disclosed for example in U.S. Pat. Nos. 3,113,225; 3,562,041; 3,733,238; 6,036,796; 6,508,641; and 6,645,330. In some configurations, the ultrasonic mechanism may be configured as a linear oscillating type sonotrode, such as for example, available from Herrmann Ultrasonic, Inc. In some configurations, the sonotrode may include a plurality of sonotrodes nested together in the cross direction CD.

As previously mentioned, the apparatus 100 described above with reference to FIGS. 1A-1HB may operate to assemble elastic laminates configured in various ways. For example, FIGS. 2A-2F show various schematic views of the apparatus 100 operating to assemble a first elastic laminate 200 and a second elastic laminate 202.

Figure 2A:
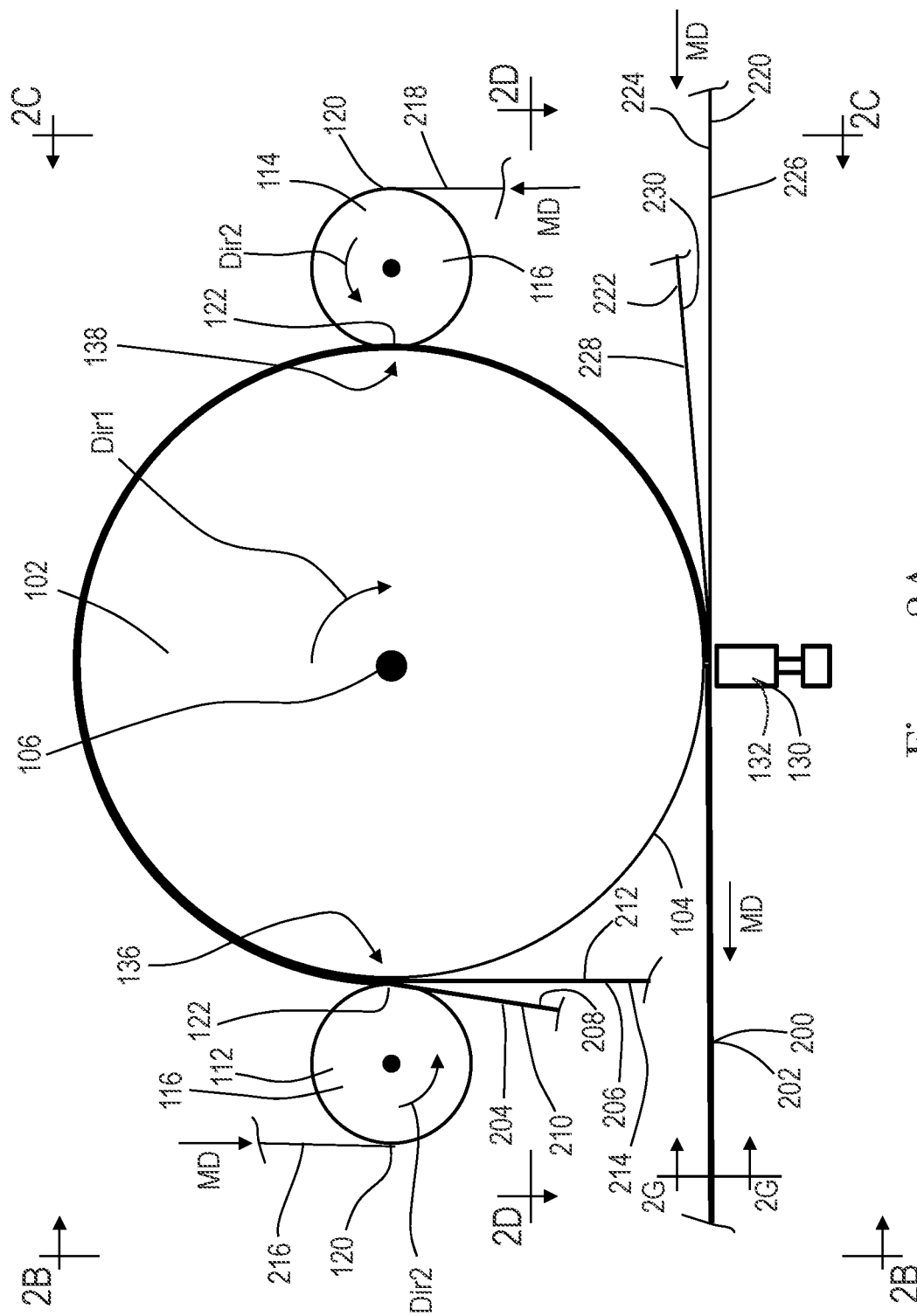
FIG. 2A is a schematic side view of an apparatus operating to assemble an elastic laminate.
Figure 2D:
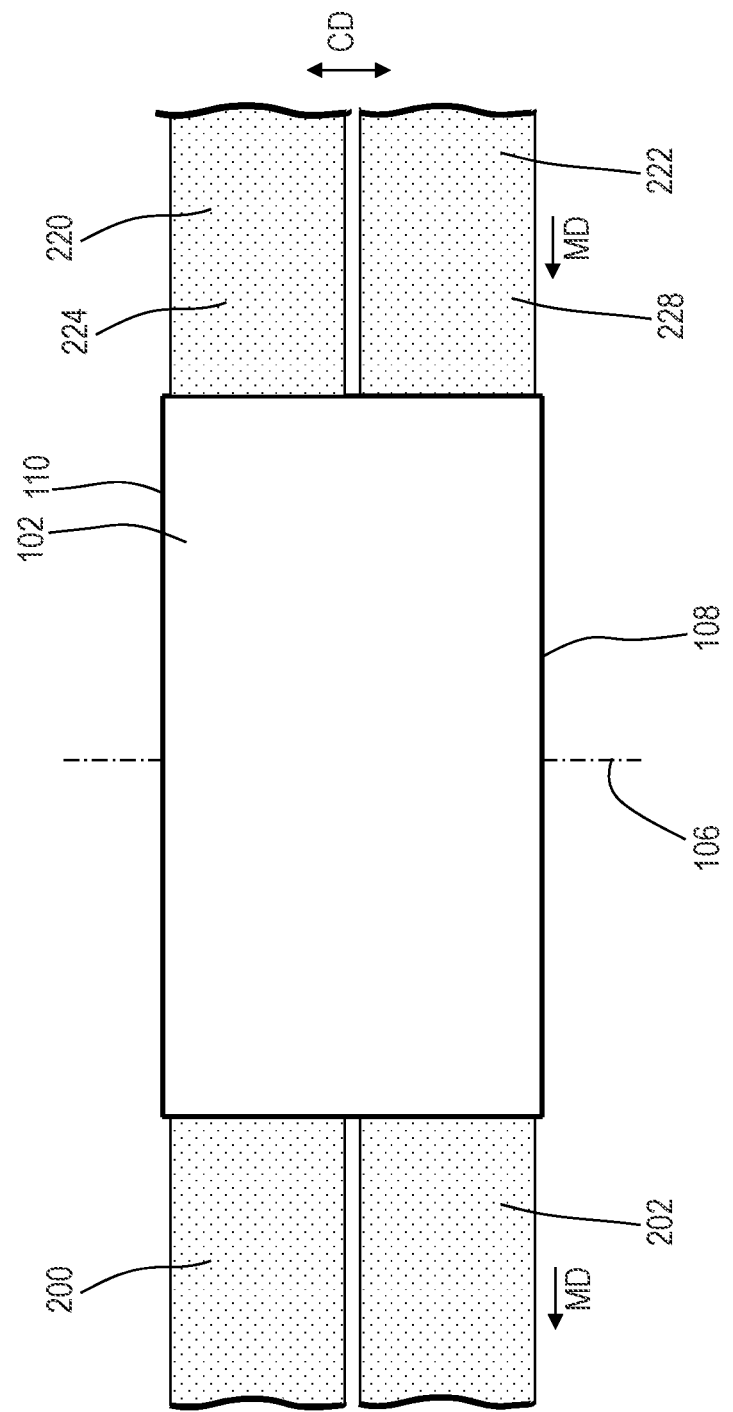
FIG. 2D is a top side view of the elastic laminates and apparatus from FIG. 2A taken along line 2D-2D.

As shown in FIGS. 2A and 2B, a first substrate 204 and a second substrate 206 advance in a machine direction MD onto the rotating anvil 102. More particularly, the first substrate 204 includes a first surface 208 and an opposing second surface 210, and the first substrate 204 advances to wrap the first surface 208 onto the outer circumferential surface 104 of the rotating anvil 102. Similarly, the second substrate 206 includes a first surface 212 and an opposing second surface 214, and the second substrate 206 advances to wrap the first surface 212 onto the outer circumferential surface 104 of the rotating anvil 102. As shown in FIG. 2B, the first substrate 204 and the second substrate 206 are separated from each other in the cross direction CD. It also to be appreciated that the first substrate 204 and the second substrate 206 may be formed by slitting a single substrate along the machine direction MD before or after advancement onto the anvil 102.

As shown in FIGS. 2A-2C, during the assembly process, a first elastic material 216 is stretched in the cross direction CD and is positioned into contact with the second surface 210 of the first substrate 204. With particular reference to FIG. 2E, the first elastic material 216 includes a first edge region 216a and a second edge region 216b separated from the first edge region 216a in the cross direction CD by a central region 216c. As shown in FIG. 2A, the first elastic material 216 advances in a machine direction MD onto the first spreader mechanism 112 at or downstream of the first location 120. In particular, the first edge region 216a of the first elastic material 216 advances onto the outer rim 116b of the first disk 116 of the first spreader mechanism 112, and the second edge region 216b advances onto the outer rim 118b of the second disk 118. As previously discussed with reference to FIG. 1E, the outer rims 116b, 118b of the first and second disks 116, 118 of the first spreader mechanism 112 may include channels 124 fluidly connected to a vacuum pressure source 129 and may include radially protruding nubs 128. Thus, as shown in FIG. 2E, the first edge region 216a of the first elastic material 216 may be held in position on the outer rim 116b with vacuum air pressure in the channels 124 and with the radially protruding nubs 128. Similarly, the second edge region 216b of the first elastic material 216 may be held in position on the outer rim 118b with vacuum air pressure in the channels 124 and with the radially protruding nubs 128.

With continued reference to FIG. 2E, as the first disk 116 and the second disk 118 of the first spreader mechanism 112 rotate, the central region 216c of the first elastic material 216 is stretched in the cross direction CD. Because the first and second edge regions 216a, 216b are held in position on the outer rims 116b, 118b, some portions of the first and second edge regions 216a, 216b may remain unstretched in the cross direction CD as the first and second disks 116, 118 rotate. Referring now to the FIGS. 2A and 2B, the first elastic material 216 advances from the first spreader mechanism 112 and is transferred onto the second surface 210 of the first substrate 204 on the anvil 102 at a first application zone 136. It is to be appreciated that during the transfer from the first spreader mechanism 112 to the anvil 102, the first elastic material 216 may be removed from the first spreader mechanism 112 at or upstream of the second location 122. As previously mentioned, the outer circumferential surface 104 of the anvil 102 may be fluidly connected with the vacuum source 105, and as such, vacuum air pressure may be applied to the first substrate 204 on the anvil 102. In addition, when the first substrate 204 is configured as a porous substrate, such as a nonwoven, vacuum air pressure may also be applied to the first elastic material 216 on the anvil 102, and as such, may help maintain the stretched condition of the central region 216c of the first elastic material 216 while on the anvil 102.

Referring now to FIGS. 2A and 2C, during the assembly process, a second elastic material 218 is stretched in the cross direction CD and is positioned into contact with the second surface 214 of the second substrate 206. With particular reference to FIG. 2F, the second elastic material 218 includes a first edge region 218a and a second edge region 218b separated from the first edge region 218a in the cross direction CD by a central region 218c. As shown in FIG. 2A, the second elastic material 218 advances in a machine direction MD onto the second spreader mechanism 114 at or downstream of the first location 120. In particular, the first edge region 218a of the second elastic material 218 advances onto the outer rim 116b of the first disk 116 of the second spreader mechanism 114, and the second edge region 218b advances onto the outer rim 118b of the second disk 118. As previously discussed with reference to FIG. 1F, the outer rims 116b, 118b of the first and second disks 116, 118 of the second spreader mechanism 114 may include channels 124 fluidly connected to a vacuum pressure source 129 and may include radially protruding nubs 128. Thus, as shown in FIG. 2F, the first edge region 218a of the second elastic material 218 may be held in position on the outer rim 116b with vacuum air pressure in the channels 124 and with the radially protruding nubs 128. Similarly, the second edge region 218b of the second elastic material 218 may be held in position on the outer rim 118b with vacuum air pressure in the channels 124 and with the radially protruding nubs 128. With continued reference to FIG. 2F, as the first disk 116 and the second disk 118 of the second spreader mechanism 114 rotate, the central region 218c of the second elastic material 218 is stretched in the cross direction CD. Because the first and second edge regions 218a, 218b are held in position on the outer rims 116b, 118b, some portions of the first and second edge regions 218a, 218b may remain unstretched in the cross direction CD as the first and second disks 116, 118 rotate. As previously mentioned, nubs 128 and/or vacuum air pressure in the channels 124 may be used to help held the elastic materials 216, 218 onto the rims 116b, 118b during operation. As such, the nubs 128 and channels 124 may be configured to help reduce widths of unstretched portions of the first and second edge regions 216a, 216b, 218a, 218b in the cross direction CD. For example, in some configurations, the widths of unstretched portions of the first and second edge regions 216a, 216b, 218a, 218b in the cross direction CD may about 3 mm or less.

As shown in FIGS. 2E and 2F, the outer rims 116b, 118b of the first and second disks 116, 118 may extend outboard in the cross direction CD from the outer edges of the elastic materials 216, 218. The extended portions of the outer rims 116b, 118b may help provide additional support for the elastic materials 216, 218 and may help prevent edge foldovers during the transition to the anvil 102. In some configurations, a series of grooves may be cut into the rims 116b, 118b help constrain the edge regions 216a, 216b, 218a, 218b of the elastic materials 216, 218.

Referring now to the FIGS. 2A and 2C, the second elastic material 218 advances from the second spreader mechanism 114 and is transferred onto the second surface 214 of the second substrate 206 on the anvil 102 at a second application zone 138. As previously mentioned, the first spreader mechanism 112 is angularly displaced from the second spreader mechanism 114 with respect to the first axis of rotation 106. As such, the second application zone 138 is positioned downstream of the first application zone 136. It is to be appreciated that during the transfer from the second spreader mechanism 114 to the anvil 102, the second elastic material 218 may be removed from the second spreader mechanism 114 at or upstream of the second location 122. As previously mentioned, the outer circumferential surface 104 of the anvil 102 may be fluidly connected with the vacuum source 105, and as such, vacuum air pressure may be applied to the second substrate 206 on the anvil 102. In addition, when the second substrate 206 is configured as a porous substrate, such as a nonwoven, vacuum air pressure may also be applied to the second elastic material 218 on the anvil 102, and as such, may help maintain the stretched condition of the central region 218c of the second elastic material 218 while on the anvil 102.

As shown in FIGS. 2A-2C, the first elastic laminate 200 may be formed by ultrasonically bonding the first substrate 204 and first elastic material 216 together with a third substrate 220 on the anvil 102, and the second elastic laminate 202 may be formed by ultrasonically bonding the second substrate 206 and second elastic material 218 together with a fourth substrate 222 on the anvil 102. More particularly, the third substrate 220 includes a first surface 224 and an opposing second surface 226, and the third substrate 220 advances to position the first surface 224 in contact with first elastic material 216 and the second surface 210 of the first substrate 204. In addition, the fourth substrate 222 includes a first surface 228 and an opposing second surface 230, and the fourth substrate 222 advances to position the first surface 228 in contact with second elastic material 218 and the second surface 214 of the second substrate 206. It is also to be appreciated that the third substrate 220 and the fourth substrate 222 may be formed by slitting a single substrate along the machine direction MD before or after advancement onto the anvil 102.

With continued reference to FIGS. 2A-2C, as the anvil 102 rotates, the first substrate 204, the first elastic material 216, and the third substrate 220 are advanced between the outer circumferential surface 104 of the anvil 102 and the ultrasonic horn 132. In addition, the second substrate 206, the second elastic material 218, and the third substrate 222 are advanced between the outer circumferential surface 104 of the anvil 102 and the ultrasonic horn 132. In turn, the ultrasonic horn 132 bonds the first substrate 204, the first elastic material 216, and the third substrate 220 together to form the first elastic laminate 200. Similarly, the ultrasonic horn 132 bonds the second substrate 206, the second elastic material 218, and the fourth substrate 222 together to form the first elastic laminate 200. As shown in FIGS. 2A, 2E, and 2G, the first elastic laminate 200 and the second elastic laminate 202 may then advance from the anvil 102. FIG. 2H also shows the first elastic laminate 200 and the second elastic laminate 202 in relaxed states wherein the central region 216c of the first elastic material 216 is contracted in the cross direction CD and wherein the central region 218c of the second elastic material 218 is contracted in the cross direction CD.

During the ultrasonic bonding process, it is to be appreciated that bonds imparted into the first and second elastic laminates 200, 202 from the ultrasonic horn 132 may correspond with patterns and/or shapes defined by the plurality of pattern elements 134 extending radially outward from the outer circumferential surface 104 of the anvil 102. It is to be appreciated that the first elastic laminate 200 may include various portions of components bonded together in various ways and with differing or identical bond patterns. For example, the unstretched portions of the first and second edge regions 216a, 216b of the first elastic material 216 may be bonded together with the first and/or third substrates 204, 220. In addition, the stretched central region 216c of the first elastic material 216 may be bonded together with the first and/or third substrates 204, 220. Further the first substrate 204 may be bonded directly to the third substrate 220 in areas of the first elastic laminate 200. It is also to be appreciated that the second elastic laminate 202 may include various portions of components bonded together in various ways and with differing or identical bond patterns. For example, the unstretched portions of the first and second edge regions 218a, 218b of the second elastic material 218 may be bonded together with the second and/or fourth substrates 206, 222. In addition, the stretched central region 218c of the second elastic material 218 may be bonded together with the second and/or fourth substrates 206, 222. Further the second substrate 206 may be bonded directly to the fourth substrate 222 in areas of the second elastic laminate 202. It is to be appreciated that the apparatus 100 may be adapted to create various types of bond configurations, such as disclosed, for example, in U.S. Pat. No. 6,572,595.

As previously mentioned, the apparatus 100 described above with reference to FIGS. 1A-1HB may operate to assemble elastic laminates configured in various ways. For example, FIGS. 3A-3F show various schematic views of the apparatus 100 operating to assemble an elastic laminate 232 that is subsequently slit along the machine direction MD into a first elastic laminate 200 and a second elastic laminate 202.

Figure 3A:
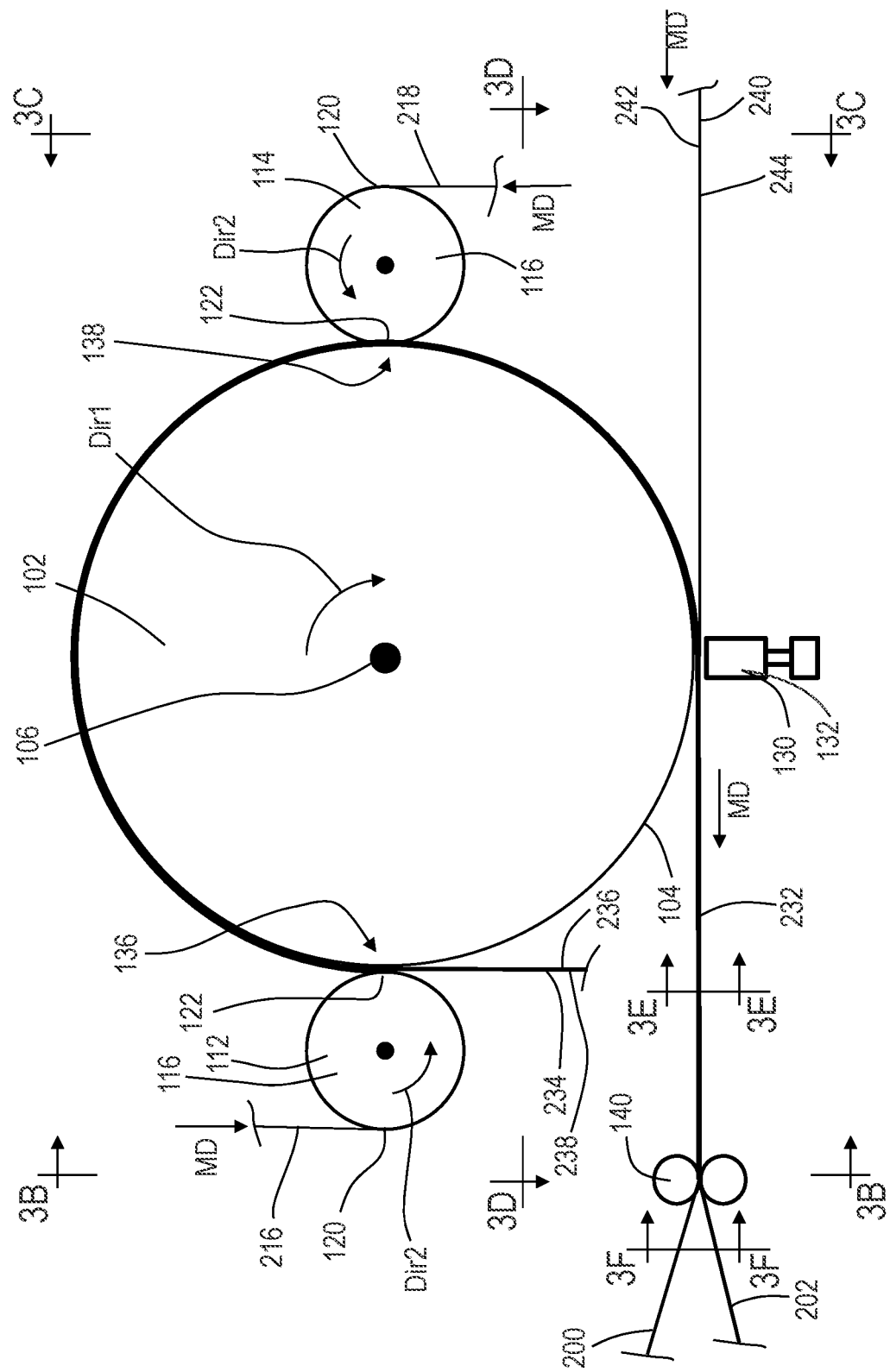
FIG. 3A is a schematic side view of an apparatus operating to assemble elastic laminates.

As shown in FIGS. 3A and 3B, a first substrate 234 advances in a machine direction MD onto the rotating anvil 102. More particularly, the first substrate 234 includes a first surface 236 and an opposing second surface 238, and the first substrate 234 advances to wrap the first surface 236 onto the outer circumferential surface 104 of the rotating anvil 102. As described above with reference to FIGS. 2A and 2E, the first elastic material 216 advances in a machine direction MD onto the first spreader mechanism 112 and is stretched in the cross direction CD. As shown in FIGS. 3A-3C, the first elastic material 216 advances from the first spreader mechanism 112 and is transferred onto the second surface 238 of the first substrate 234 on the anvil 102 at the first application zone 136. As shown in FIG. 3B, the first substrate 234 may be wider than the first elastic material 216 along the cross direction CD. As described above with reference to FIGS. 2A and 2F, the second elastic material 218 advances in a machine direction MD onto the second spreader mechanism 114 and is stretched in the cross direction CD. As shown in FIGS. 3A and 3C, the second elastic material 218 advances from the second spreader mechanism 114 and is transferred onto the second surface 238 of the first substrate 234 on the anvil 102 at the second application zone 138. The second elastic material 218 may be axially separated or spaced from the first elastic material 216 in the cross direction CD such that a cross directional gap exists between the first elastic material 216 and the second elastic material 218.

As shown in FIGS. 3A-3C, an elastic laminate 232 may be formed by ultrasonically bonding the first substrate 234, the first elastic material 216, and the second elastic material 218 together with a second substrate 240 on the anvil 102. More particularly, the second substrate 240 includes a first surface 242 and an opposing second surface 244, and the second substrate 240 advances to position the first surface 242 in contact with first elastic material 216, the second elastic material 218, and the second surface 238 of the first substrate 234. As the anvil 102 rotates, the first substrate 234, the first elastic material 216, the second elastic material 218, and the second substrate 240 are advanced between the outer circumferential surface 104 of the anvil 102 and the ultrasonic horn 132. In turn, the ultrasonic horn 132 bonds the first substrate 234, the first elastic material 216, and the second substrate 240 together and also bonds the first substrate 234, the second elastic material 218, and the second substrate 240 together to form the elastic laminate 232, such as shown in FIG. 3E.

Figure 3D:
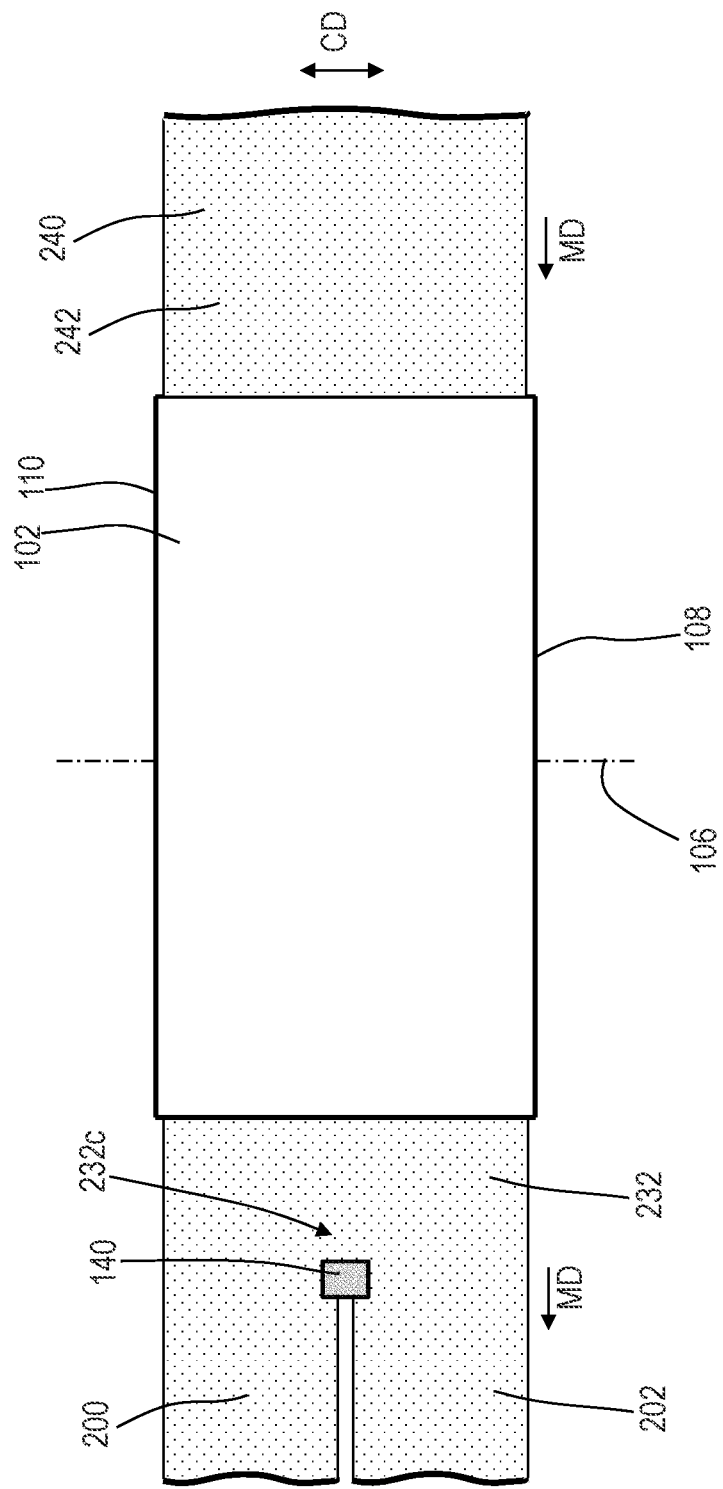
FIG. 3D is a top side view of the elastic laminate and apparatus from FIG. 3A taken along line 3D-3D.

As shown in FIGS. 3A and 3D, the elastic laminate 232 may then advance from the anvil 102 to a cutter 140. In turn, the cutter 140 separates the elastic laminate 232 into the first elastic laminate 200 and the second elastic laminate 202. It is to be appreciated that the cutter 140 may be configured in various ways. For example, in some embodiments the cutter 140 may be a slitter or a die cutter that separates the elastic laminate 232 into the first elastic laminate 200 and the second elastic laminate with either a straight line cut and/or a curved line cut extending in machine direction MD. The cutter 140 may also be configured as a perforator that perforates the elastic laminate 232 with a line of weakness and wherein the elastic laminate 232 is separated along the line of weakness in a later step. It is also to be appreciated that the cutter 140 may be configured to cut elastic laminate 232 into the first and second elastic laminates 200, 202 while the elastic laminate 232 is positioned on the anvil 104.

In some configurations, the cutter 140 may cut the elastic laminate 232, such as shown in FIG. 3E along a line extending in the machine direction MD through a central region or location 232c of the elastic laminate 232. As such, the elastic laminate 232 may be separated into the first elastic laminate 200 and the second elastic laminate 202, such as shown in FIG. 3F. After slitting the elastic laminate 232, the first elastic laminate 200 and the second elastic laminate 202 may be allowed to relax or contract in the cross direction CD, wherein the central region 216c of the first elastic material 216 is contracted in the cross direction CD and wherein the central region 218c of the second elastic material 218 is contracted in the cross direction CD, such as shown in FIG. 3G. In some configurations, such as shown in FIG. 3H, the elastic laminate 232 may be allowed to relax or contract in the cross direction CD before being separated by the cutter 140 into the first elastic laminate 200 and the second elastic laminate 202 such as shown in FIG. 3G.

As shown in FIGS. 3E and 3H, the central region or location 232c of the elastic laminate 232 may be defined by an area between the first elastic material 216 and the second elastic material 218 where first substrate 234 and the second substrate 240 are bonded directly to each other. As such, slitting the elastic laminate 232 with the cutter 140 along the central region 232c may eliminate the need to also cut through the first elastic material 216 and/or the second elastic material 218 when creating the first and second elastic laminates 200, 202. As such, the slit edges of the first and second elastic laminates 200, 202 may not have exposed elastic material 216, 218 and thus, may be relatively more aesthetically pleasing.

It is to be appreciated that aspects of the apparatus 100 herein may be configured to assemble elastic laminates from various types of material and/or components. For example, it is to be appreciated that the first substrate 204, the second substrate 206, the third substrate 220, and/or the fourth substrate 222 discussed above with reference to FIGS. 2A-2HB may be configured as the same or different types of materials. Similarly, it is to be appreciated that the first substrate 234 and the second substrate 240 discussed above with reference to FIGS. 3A-3H may be configured as the same or different types of materials. For example, the substrates 204, 206, 220, 222, 234, 240 may be configured as single layer or multi-layer nonwovens. In some examples wherein the elastic laminates 200, 202 may be used to manufacture diaper components, the substrates 204, 206, 234 may define garment facing surfaces of the elastic laminates 200, 202 in diaper components, whereas the substrates 220, 222, 240 may define body facing surfaces of the elastic laminates 200, 202 in diaper components. As such, the substrates 204, 206, 234 may be configured as a relatively high cost, premium material for aesthetic purposes, such as soft feel and appearance. In contrast, the substrates 220, 222, 240 may be configured as a cost optimized nonwoven, a premium nonwoven marketed as soft against a wearer's skin, or a high coefficient of friction nonwoven for improved fit. In some examples, the substrates may be configured as a relatively low basis weight nonwoven intended define a wearer facing surface, which may help to reduce the changes of pressure marks on the baby's skin from corrugations in the elastic laminates. A relatively low basis weight nonwoven may also have a relatively low bending stiffness, and thus any corrugations against the wearer's skin collapse at a relatively lower forces.

As previously mentioned the first and second elastic materials 216, 218 may be configured in various ways and from various materials. For example, the elastic materials may be formed by any suitable method in the art, for example, by extruding molten thermoplastic and/or elastomeric polymers or polymer blends through a slit die and subsequently cooling the extruded sheet. Other non-limiting examples for making film forms include casting, blowing, solution casting, calendaring, and formation from aqueous or, non-aqueous cast dispersions. The elastomer composition of the present invention may be made into a film having a basis weight of from about 5 to about 150 g/m$^2$. The elastic material can also be an apertured film made of elastomeric material to provide breathability. In some configurations, the first and second elastic materials include a nonwoven web of synthetic fibers. The web can be made of fibers from elastomers or can be mixture of elastomeric fibers with plastic fibers. The first and second elastic materials may also be configured as laminates including elastic material connected with and/or interposed between an outer layer and an inner layer. The elastic material may include one or more elastic elements such as strands, ribbons, or panels. Suitable elastomeric compositions for making elastic materials comprise thermoplastic elastomers selected from the group consisting of Styrenic block copolymers, poly-esters, polyurethanes, polyether amides, polyolefin elastomers, and combinations thereof.

It is to be appreciated that aspects of the apparatus 100 herein may be configured in various ways and may operate to assemble elastic laminates 200, 202 from various types of material and/or components. For example, it is to be appreciated that the in some configurations, the elastic laminate assembly operations may be performed separate to a final assembly process, such as for example, assembling the elastic laminates offline wherein the elastic laminates may be stored until needed for production. For example, elastic laminate assembly operations may be accomplished on discrete assembly lines, separately from converting lines that may be dedicated to manufacturing disposable absorbent articles. After assemblage on the discrete lines, the elastic laminates may be delivered to the absorbent article converting lines, such as in a form of rolls of continuous elastic laminates. It is to be appreciated that such rolls of continuous elastic laminates may be planetary wound or traversely wound. It is also appreciated that the elastic laminate assembly process may be done online during the article assembly process.

As discussed above, the first spreader mechanism 112 and the second spreader mechanism 114 are axially and angularly displaced from each other with respect to the axis of rotation 106 of the anvil 102. Because the first spreader mechanism 112 is angularly displaced from the second spreader mechanism 114 with respect to the first axis of rotation 106, the distance in the cross direction CD between the second disk 118 of the first spreader mechanism 112 and the first disk 116 of the second spreader mechanism 114 may be minimized without physical interference between the spreader mechanisms 112, 114. In turn, the distance in the cross direction CD between inboard edges of the first elastic material 216 and second elastic material 218 on the anvil 102 may be minimized.

It is also to be appreciated that aspects of the spreader mechanisms 112, 114 may be configured to be independently controlled. For example, the cross direction CD positions of the spreader mechanisms 112, 114 relative to each other and/or the anvil 102 may be adjustable. In addition, the cross direction CD positions of the disks 116, 118 of each of the spreader mechanisms 112, 114 may be adjustable relative to each other. In addition, canting angles of the disks 116, 118 of each of the spreader mechanisms 112, 114 may be adjustable. The canting angle of the first disk 116 may be defined as an angular offset between the axis of rotation 116a of the first disk 116 and the axis of rotation 106 of the anvil 102, and the canting angle of the second disk 118 may be defined as an angular offset between the axis of rotation 118a of the second disk 118 and the axis of rotation 106 of the anvil 102. In some configurations, radial clearances between the outer circumferential surface 104 of the anvil 102 and the outer rims 116b, 118b of the first and second disks 116, 118 of the first and/or second spreader mechanisms 112, 114 may be adjustable, wherein the positions of the disks 116, 118 may be configured to be independently or collectively adjustable. In some configurations, the radial clearance between the outer circumferential surface 104 of the anvil 102 and the outer rims 116b, 118b may be zero or greater than zero.

It is to be appreciated that various drives may be used to control the rotation of the disks 116, 118 of the first spreader mechanism 112 and/or the second spreader mechanism 114. For example, the disks 116, 118 of the first spreader mechanism 112 and/or the second spreader mechanism 114 may be driven by one or more motors, such as a servo motor. In some configurations, motors may be directly connected with the disks 116, 118, and in some configurations, motors may be indirectly connected with the disks 116, 118, such as through belts, pulleys, and/or gears. The disks 116, 118 may be driven as a pair through the use of a common driveshaft with a coupling between the disks. In some configurations, a common jackshaft may be used to drive both disks 116, 118 together with a single motor. In some configurations, drives of the anvil 102 and spreader mechanisms 112, 114 may be operatively connected, and may be configured with a single motor. In some configurations, the disks 116, 118 of the first spreader mechanism 112 and/or the second spreader mechanism 114 may be driven only by the advancement of the first elastic material 216 and second elastic material 218. In some configurations, the disks 116, 118 of the first spreader mechanism 112 and/or the second spreader mechanism 114 may be driven by rotation of the anvil 102 or an infeed idler. Other drives may include surface driving through a jackshaft with a friction material in operative contact with disks 116, 118.

As discussed above, the disks 116, 118 of the first spreader mechanism 112 and/or the second spreader mechanism 114 may include various quantities of nubs 128 that protrude radially outward from the rims 116b, 118b, wherein the nubs 128 may help prevent the edge regions of the elastic materials from sliding along the rims 116b, 118b while stretching the elastic materials 216, 218. It is to be appreciated that the nubs 128 may be configured in various shapes and sizes, spacing, and may be constructed from various types of materials. In some configurations, the nubs 128 may be configured with a radial height of about 0.85 mm and a cross directional width of about 0.70 mm. In addition, the nubs 128 may be arranged to be spaced apart from each other by about 4 mm. In some configurations, the nubs 128 may be made from a relatively soft material, such as polyurethane. As such, nubs 128 made from a relatively soft material may help reduce occurrences wherein nubs 128 pierce the elastic materials 216, 218. In addition, nubs 128 made from a relatively soft material may be sacrificed in the event of unintended contact between the nubs 128 and pattern elements 134 on the anvil 102 while protecting the pattern elements 134 from damage. In some configurations, the nubs 128 may be made from a relatively hard material, such as steel, and the support members 126 extending across the channels 124 may be made from a relatively soft material.

As discussed above, the disks 116, 118 of the first spreader mechanism 112 and/or the second spreader mechanism 114 may include channels 124 extending radially inward from the rims 116b, 118b, wherein the channels 124 may be fluidly connected with a vacuum pressure source 129. It is to be channels and vacuum pressure source may be configured in various ways to help hold the elastic materials 216, 218 in position on the disks 116, 118 and/or help transfer the elastic materials 216, 218 to the anvil 102. For example, in some configurations, the channels 124 may be a single slot broken into segments by commutator elements, which define a plurality of consecutive vacuum chambers. Each segment may then be controlled for the on and off timing of vacuum as the disks 116, 118 rotate. Each segment or a plurality of segments may also be selected for a blow-off function at an angle of rotation of the disks 116, 118 help the transfer of the elastic materials 216, 218 from the disks 116, 118 to the anvil 102. Blow-off may also be used to clean the ports, or prevent the wrapping of the elastic materials 216, 218 on the disks 116, 118. Such blow-off may be configured as a venting of a vacuum chamber by opening a port to atmosphere. In some configurations, such blow-off may be configured as a positive air pressure, such as from a compressed air line. In some configurations, the disks 116, 118 may be connected with one or more vacuum hoses. For example, one of the vacuum hoses may be provided adjacent the first and/or second application zones 136, 138, which may help ensure sufficient static pressure to operatively grip the elastic materials 216, 218 with the disks 116, 118, even when a substantial amount of the channels 124 are exposed to atmospheric pressure. A flow limiting device, such as a venturi element, may be used to restrict the maximum volumetric flow rate of air in the vacuum manifold. Such flow restriction may function to ensure sufficient static pressure is available to operatively engage the elastic materials 216, 218 with the disks. The flow limiting device may be configured as a small diameter port or tube, such as a 3 mm diameter tube, intermediate the vacuum plenum and channels 124 which operatively engages the elastic materials 216, 218. Such contraction may be of a small length in the MD and may have chamfered or curved edges, both of which may serve to minimize pressure drop. The pressure in the vacuum system may range from about 2 kPa to about 20 kPa. In some configurations, the vacuum system may operate in the range of about 12 kPa to about 16 kPa or higher. The width of the channels 124 in the cross direction CD may be from about 0.7 mm to about 2.0 mm, and may be from about 1.4 mm to about 1.7 mm wide. In some configurations, the combined widths of the nubs 128 and the channels 124 in the cross direction CD may be from about 1 mm to about 7 mm, and may be about 1.5 mm to about 2 mm.

As previously mentioned, the anvil 102, and more particularly, the outer circumferential surface 104 may be fluidly connected with a vacuum source 105, wherein vacuum air pressure may be used to help held the substrates and elastic materials onto the outer circumferential surface 104 during operation. Thus, in some configurations, the outer circumferential surface 104 may include a pattern of vacuum holes. Such a pattern may allow a wide variety of film widths and cross direction placements with a single anvil. The anvil 102 may also include a plurality of internal tubes to define one or more vacuum regions on outer circumferential surface 104. In some configurations, each tube may have a first vacuum region adjacent inboard edges of the elastic materials 216, 218, and a second vacuum region adjacent outboard edges of the elastic materials 216, 218. In some configurations, the vacuum regions may be externally adjustable.

Figure 4B:
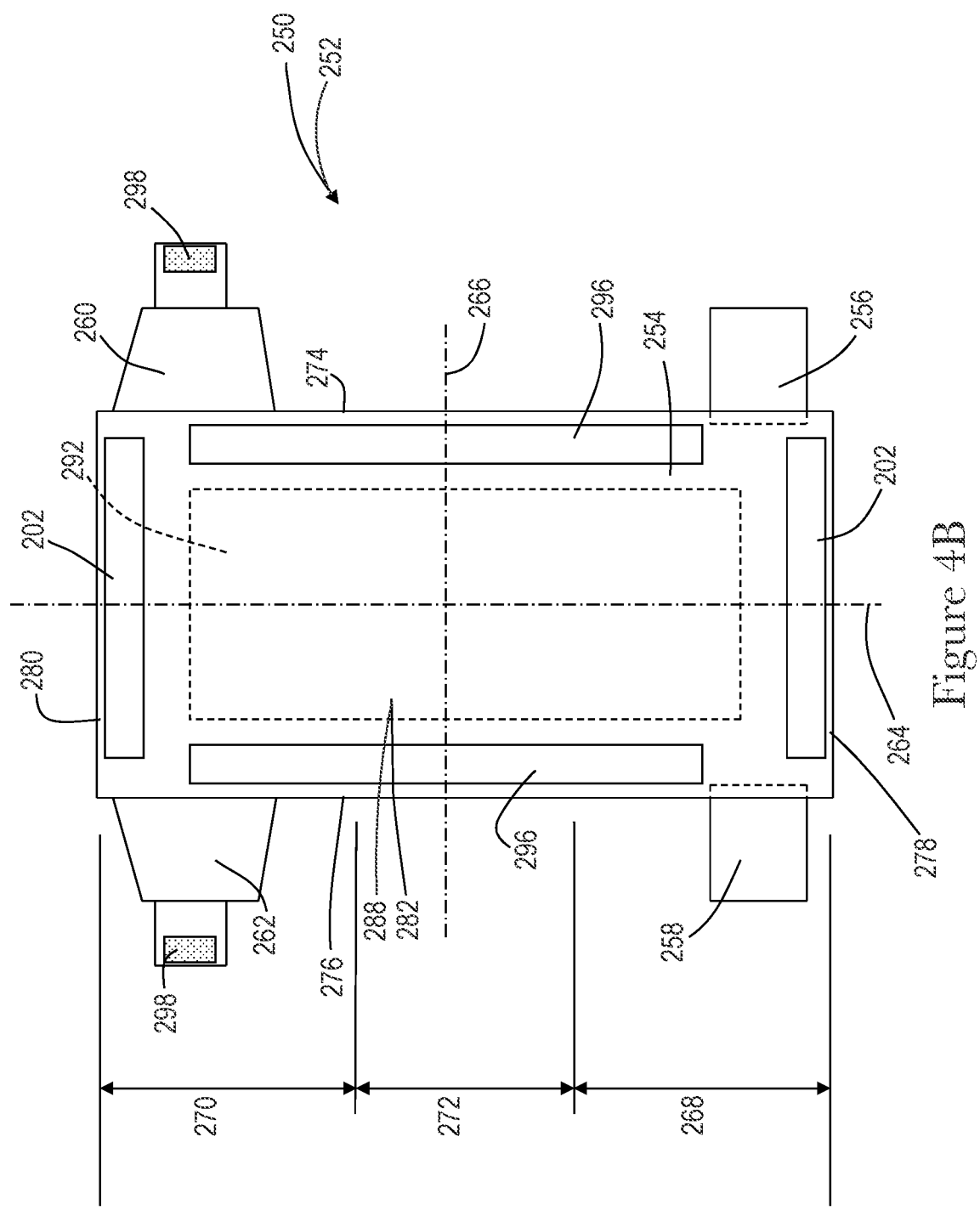
FIG. 4B is a plan view of the absorbent article of FIG. 4A that may include one or more elastic laminates manipulated during manufacture according to the apparatuses and methods disclosed herein with the portion of the diaper that faces toward a wearer oriented towards the viewer.

As mentioned above, apparatuses and methods of the present disclosure may be utilized to assembly various forms of elastic laminates used in the manufacture of absorbent articles. Such elastic laminates may be utilized in absorbent article components such as, for example: backsheets, topsheets, absorbent cores, front and/or back ears, fastener components, and various types of elastic webs and components such as leg elastics, barrier leg cuff elastics, and waist elastics. For the purposes of a specific illustration, FIGS. 4A and 4B show an example of a disposable absorbent article 250 in the form of a diaper 252 that may be constructed from such elastic laminates manipulated during manufacture according to the apparatuses and methods disclosed herein. In particular, FIG. 4A is a partially cut away plan view of an absorbent article in the form of a taped diaper that may include one or more elastic laminates assembled during manufacture according to the apparatuses and methods disclosed herein with the portion of the diaper that faces away from a wearer oriented towards the viewer. FIG. 4B is a plan view of the absorbent article of FIG. 4A that may include one or more elastic laminates assembled during manufacture according to the apparatuses and methods disclosed herein with the portion of the diaper that faces toward a wearer oriented towards the viewer.

As shown in FIGS. 4A-4B, the diaper 252 includes a chassis 254 having a first ear 256, a second ear 258, a third ear 260, and a fourth ear 262. To provide a frame of reference for the present discussion, the chassis is shown with a longitudinal axis 264 and a lateral axis 266. The chassis 254 is shown as having a first waist region 268, a second waist region 270, and a crotch region 272 disposed intermediate the first and second waist regions. The periphery of the diaper is defined by a pair of longitudinally extending side edges 274, 276; a first outer edge 278 extending laterally adjacent the first waist region 268; and a second outer edge 280 extending laterally adjacent the second waist region 270. As shown in FIGS. 4A-4B, the chassis 254 includes an inner, body-facing surface 282, and an outer, garment-facing surface 284. A portion of the chassis structure is cut-away in FIG. 4A to more clearly show the construction of and various features that may be included in the diaper. As shown in FIGS. 4A-4B, the chassis 254 of the diaper 252 may include a topsheet 288 defining the inner, body-facing surface 282, and a backsheet 290 defining the outer, garment-facing surface 284. An absorbent core 292 may be disposed between a portion of the topsheet 288 and the backsheet 290. As discussed in more detail below, any one or more of the regions may be stretchable and may include an elastomeric material or laminate as described herein. As such, the diaper 252 may be configured to adapt to a specific wearer's anatomy upon application and to maintain coordination with the wearer's anatomy during wear.

The absorbent article 250 may also include an elastic waist feature 202 shown in FIG. 4B in the form of a waist band and may provide improved fit and waste containment. The elastic waist feature 202 may be configured to elastically expand and contract to dynamically fit the wearer's waist. The elastic waist feature 202 can be incorporated into the diaper and may extend at least longitudinally outwardly from the absorbent core 292 and generally form at least a portion of the first and/or second outer edges 278, 280 of the diaper 252. In addition, the elastic waist feature may extend laterally to include the ears. While the elastic waist feature 202 or any constituent elements thereof may comprise one or more separate elements affixed to the diaper, the elastic waist feature may be constructed as an extension of other elements of the diaper, such as the backsheet 290, the topsheet 288, or both the backsheet and the topsheet. In addition, the elastic waist feature 202 may be disposed on the outer, garment-facing surface 284 of the chassis 254; the inner, body-facing surface 282; or between the inner and outer facing surfaces. The elastic waist feature 202 may be constructed in a number of different configurations including those described in U.S. Patent Publication Nos. US2007/0142806A1; US2007/0142798A1; and US2007/0287983A1, all of which are hereby incorporated by reference herein.

As shown in FIGS. 4A-4B, the diaper 252 may include leg cuffs 296 that may provide improved containment of liquids and other body exudates. In particular, elastic gasketing leg cuffs can provide a sealing effect around the wearer's thighs to prevent leakage. It is to be appreciated that when the diaper is worn, the leg cuffs may be placed in contact with the wearer's thighs, and the extent of that contact and contact pressure may be determined in part by the orientation of diaper on the body of the wearer. The leg cuffs 296 may be disposed in various ways on the diaper 202.

The diaper 252 may be provided in the form of a pant-type diaper or may alternatively be provided with a re-closable fastening system, which may include fastener elements in various locations to help secure the diaper in position on the wearer. For example, fastener elements 298 may be located on the ears and may be adapted to releasably connect with one or more corresponding fastening elements located in the first or second waist regions. For example, as shown in FIG. 4A, the diaper 252 may include a connection zone 282, sometimes referred to as a landing zone, in the first waist region 268. It is to be appreciated that various types of fastening elements may be used with the diaper.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. An apparatus for making elastic laminates, the apparatus comprising:
   an anvil comprising an outer circumferential surface and adapted to rotate in a first direction about an axis of rotation, a plurality of pattern elements extending radially outward from the outer circumferential surface, the anvil extending axially from a first end to a second end;
   an ultrasonic horn adjacent the outer circumferential surface;

a first spreader mechanism comprising a first disk and a second disk, the first disk axially displaced from the second disk along the axis of rotation, wherein the first disk and the second disk are canted relative each other, each disk comprising an outer rim, the first and second disks adapted to rotate in a second direction opposite the first direction;

a second spreader mechanism comprising a first disk and a second disk, the first disk axially displaced from the second disk along the axis of rotation, wherein the first disk and the second disk are canted relative to each other, each disk comprising an outer rim, the first and second disks adapted to rotate in a second direction opposite the first direction;

wherein the first spreader mechanism is axially displaced from the second spreader mechanism along the first axis of rotation; and wherein the first spreader mechanism is angularly displaced from the second spreader mechanism with respect to the first axis of rotation.

2. The apparatus of claim 1, wherein each rim of the first disk and the second disk of the first spreader mechanism comprises a channel extending radially inward.

3. The apparatus of claim 2, wherein each rim of the first disk and the second disk of the first spreader mechanism comprises a plurality of nubs extending radially outward from the rims of the first disk and the second disk, the nubs positioned axially inboard of the channel.

4. The apparatus of claim 2, comprising a vacuum pressure source fluidly connected with at least one of the channel of the first disk and the channel of the second disk.

5. The apparatus of claim 2, comprising support members extending axially across at least one of the channel of the first disk and the channel of the second disk.

6. The apparatus of claim 1, comprising a first application zone, wherein a first elastic material is advanced onto the anvil and is positioned in contact with a second surface of a first substrate.

7. The apparatus of claim 6, comprising a second application zone, wherein a second elastic material is advanced onto the anvil and is positioned in contact with the second surface of the first substrate.

8. The apparatus of claim 7, wherein the second application zone is downstream of the first application zone.

9. The apparatus of claim 7, wherein the first elastic material is separated by the second elastic material in a cross direction.

10. The apparatus of claim 7, wherein the first substrate, the first elastic material, and the second elastic material are advanced between the outer circumferential surface of the anvil and the ultrasonic horn.

11. An apparatus for stretching elastic material, the apparatus comprising:
a first disk adapted to rotate about a first axis of rotation, the first disk comprising:
an outer rim;
a channel extending radially inward from the rim;
a plurality of nubs extending radially outward from the rim, wherein the nubs are positioned axially inboard of the channel;
a second disk adapted to rotate about a second axis of rotation, the second disk axially displaced from the first disk, and wherein the first disk and the second disk are canted relative to each other, the second disk comprising:
an outer rim;
a channel extending radially inward from the rim;
a plurality of nubs extending radially outward from the rim, wherein the nubs are positioned axially inboard of the channel; and
a vacuum pressure source fluidly connected with at least one of the channels.

12. The apparatus of claim 11, wherein the first disk comprises support members extending axially across the channel.

13. The apparatus of claim 11, wherein the second disk comprises support members extending axially across the channel.

14. The apparatus of claim 11, wherein the first disk and the second disk are canted relative to each other such that a first distance exists between first portions of the first and second outer rims at a first location and such that a second, larger distance exists between second portions of the first and second outer rims at a second, different location.

15. The apparatus of claim 11, wherein the vacuum pressure is in the range of about 2 kPa to about 20 kPA.

16. The apparatus of claim 11, wherein a cross-machine directional width of one of the first and second channels is in the range of about 0.7 mm to about 2 mm.

17. The apparatus of claim 11, wherein a combined cross-machine directional width of one of the first plurality of nubs and the channel is in the range of about 1 mm to about 7 mm.

18. An apparatus for spreading an elastic material in a cross-machine direction, the apparatus comprising:
a first disk comprising a first outer rim; and
a second disk comprising a second outer rim,
wherein the first disk and the second disk are canted relative to each other,
wherein the first outer rim comprises:
a first channel defined in the first outer rim, a first plurality of support members planar with a first surface of the first outer rim and extending over portions of the first channel, and a row of a first plurality of nubs extending radially outwardly from the first surface of the first outer rim;
wherein the second outer rim comprises:
a second channel defined in the second outer rim, a second plurality of support members planar with a second surface of the second outer rim and extending over portions of the second channel, and a row of a second plurality of nubs extending radially outwardly from the second surface of the second outer rim; and
a vacuum pressure source fluidly connected the first and second channels.

19. The apparatus of claim 18, comprising additional nubs extending radially outward from the first surface of the first outer rim, and wherein the additional nubs may be positioned at least one of inboard and outboard of the first channel.

20. The apparatus of claim 18, wherein the first disk comprises a plurality of vacuum chambers such that the channel has a plurality of segments such that the vacuum pressure is individually controlled in each of the plurality of segments.

* * * * *